US009650329B2

(12) United States Patent
Biju et al.

(10) Patent No.: US 9,650,329 B2
(45) Date of Patent: May 16, 2017

(54) TRANSITION-METAL-FREE N-ARYLATION OF TERTIARY AMINES USING ARYNES

(71) Applicant: Council of Scientific and Industrial Research, New Delhi (IN)

(72) Inventors: Akkattu Thankappan Biju, Pune (IN); Sachin Suresh Bhojgude, Pune (IN); Trinadh Kaicharla, Pune (IN)

(73) Assignee: COUNCIL OF SCIENTIFIC & INDUSTRIAL RESEARCH, New Dehli (IN)

( * ) Notice: Subject to any disclaimer, the term of this patent is extended or adjusted under 35 U.S.C. 154(b) by 0 days.

(21) Appl. No.: 14/901,111

(22) PCT Filed: Jun. 24, 2014

(86) PCT No.: PCT/IN2014/000418
§ 371 (c)(1),
(2) Date: Dec. 28, 2015

(87) PCT Pub. No.: WO2014/207761
PCT Pub. Date: Dec. 31, 2014

(65) Prior Publication Data
US 2016/0137587 A1    May 19, 2016

(30) Foreign Application Priority Data
Jun. 25, 2013  (IN) .......................... 1871/DEL/2013

(51) Int. Cl.
*C07D 333/22* (2006.01)
*C07C 209/60* (2006.01)
*C07D 317/66* (2006.01)
*C07C 303/02* (2006.01)
*C07D 333/20* (2006.01)
*C07C 213/08* (2006.01)
*C07C 221/00* (2006.01)
*C07C 253/30* (2006.01)
*C07F 9/40* (2006.01)
*C07C 309/88* (2006.01)

(52) U.S. Cl.
CPC .......... *C07C 209/60* (2013.01); *C07C 213/08* (2013.01); *C07C 221/00* (2013.01); *C07C 253/30* (2013.01); *C07C 303/02* (2013.01); *C07C 309/88* (2013.01); *C07D 317/66* (2013.01); *C07D 333/20* (2013.01); *C07D 333/22* (2013.01); *C07F 9/4021* (2013.01); *C07F 9/4056* (2013.01)

(58) Field of Classification Search
CPC .................................... C07C 209/60

USPC ........................................... 549/74
See application file for complete search history.

(56) References Cited

FOREIGN PATENT DOCUMENTS

WO    WO2014/207761    12/2014

OTHER PUBLICATIONS

Okuma et al. Bull. Chem. Soc. Jpn. vol. 84, No. 3, 328-332 (2011).*
"International Application No. PCT/IN2014/000418, International Search Report mailed Oct. 20, 2014", (Oct. 20, 2014), 3 pgs.
"International Application Serial No. PCT/IN2014/000418, Written Opinion mailed Nov. 20, 2014", 6 pgs.
Bhojgude, Sachin S., "Employing Arynes in Transition-Metal-Free Monoarylation of Aromatic Tertiary Amines", Organic Letters. 15(21), (2013), 5452-5455.
Cant, Alastair A., et al., "The Benzyne Aza-Claisen Reaction", Angew. Chem. Int. Ed., 48(28), (2009), 5199-5202.
Cant, Alastair A., et al,, "The Benzyne Aza-Claisen Reaction", Angew. Chem. Int, Ed., 48(28), Correction, (2009), 1 pg.
Guram, Anil S., et al., "A Simple Catalytic Method for the Conversion of Aryl Bromides to Arylamines", Angew. Chem. Int. Ed. Engl., 34(12), (1995), 1348-1350.
Jeganmohan, Masilamani, et al., "Synthesis of N-Arylated 1,2-Dihydroheteroaromatics Through the Three-Component Reaction of Arynes with N-Heteroaromatics and Terminal Alkynes or Ketones", Chemistry—An Asian Journal, 5(1), (2010), 153-159.
Liu, Zhijian, et al., "Facile N-Arylation of Amines and Sulfonamides and O-Arylation of Phenols and Arenecarboxylic Acids", J. Org. Chem., 71(8), (2006), 3198-3209.
Louie, Janis, et al., "Palladium-Catalyzed Synthesis of Arylamines from Aryl Halides. Mechanistic Studies Lead to Coupling in the Absence of Tin Reagents", Tetrahedron Letters, 36(21), (1995), 3609-3612.
Mesganaw, Tehetena, et al., "Nickel-catalyzed amination of aryl carbamates and sequential site-selectivecross-couplings", Chem. Sci., 2, (2011), 1766-1771.
Mohanan, Kishor, et al., "Transition-Metal-Free α-Arylation of β-Keto Amides via an Interrupted Insertion Reaction of Arynes", Organic Letters, 14(17), (2012), 4686-4689.
Yoshida, Hiroto, et al., "Three-Component Coupling of Arynes, Aminosilanes, and Aldehydes", Organic Letters, 9(17), (2007), 3367-3370.

* cited by examiner

*Primary Examiner* — Nizal Chandrakumar
(74) *Attorney, Agent, or Firm* — Schwegman Lundberg & Woessner, P.A.

(57) ABSTRACT

The present invention relates to transition-metal-free process for the synthesis of tertiary arylamines comprises coupling reaction between arynes and N,N-dimethyl aniline compounds in presence of 18-crown-6, KF and THF.

6 Claims, 2 Drawing Sheets

TRANSITION-METAL-FREE N-ARYLATION OF TERTIARY AMINES USING ARYNES

PRIORITY CLAIM TO RELATED APPLICATIONS

This application is a U.S. national stage application filed under 35 U.S.C. §371 from International Application Serial No. PCT/IN2014/000418, which was filed 24 Jun. 2014, and published as WO2014/207761 on 31 Dec. 2014, and which claims priority to India Application No. 1871/DEL/2013, filed 25 Jun. 2013, which applications and publication are incorporated by reference as if reproduced herein and made a part hereof in their entirety, and the benefit of priority of each of which is claimed herein.

FIELD OF THE INVENTION

The invention relates to transition-metal-free N-arylation of tertiary amines using arynes. More particularly, present invention relates to coupling reaction between arynes generated in situ from 2-(trimethylsilyl)-aryl trifluoromethyl sulphonate of formula II and tertiary amines of formula III leading to transition-metal-free synthesis of tertiary arylamines of general formula I.

BACKGROUND AND PRIOR ART OF THE INVENTION

Arylamines are of considerable importance in a variety of industries. As such, the development of new and more general methods for their preparation is of significant interest. There is ample literature available on preparation of arylamines under catalytic conditions. The catalysts normally used in the synthesis are transition metal catalysts like Tin, Palladium and Copper.

Establishing an efficient, reliable method for the N-arylation of amines is currently a very active area of research in organic synthesis. Such aryl subunits are commonly found in a variety of biologically active and natural compounds, agrochemicals, HIV-protease inhibitors, and also compounds of interest in material science. Traditionally, the N-arylation of amines has been carried out under copper-mediated Ullmann-type conditions involving the coupling of amines with aryl halides. Although these copper-promoted reactions are useful, they usually require harsh reaction conditions and stoichiometric amounts of copper, and the yields are not very reproducible.

Article titled, "Palladium-Catalyzed Synthesis of Arylamines from Aryl Halides. Mechanistic Studies Lead to Coupling in the Absence of Tin Reagents" by Janis Louie and John F. Hartwig in *Tetrahedron Letters,* 1995, Vol. 36, No. 21, pp. 3609-3612 reports a reaction of aryl halides with secondary amines in the presence of silylamide base and tri-o-tolyphopshine palladium complexes to give arylamine products. This process provides a convenient method for performing this heterocross coupling reactions without the necessity for forming tin amides and disposing of tin halides. Further, it reports that this reaction follows from a mechanistic analysis of the coupling reaction with tin amides and occurs as a result of the cleavage of palladium aryl halide dimers with secondary amines.

Article titled, "A Simple Catalytic Method for the Conversion of Aryl Bromides to Arylamines" by Anil S. Guram, Roger A. Rennels, and Stephen L. Buchwald in Angew. *Chem. Int. Ed. Engl.* 1995, 34. Issue No. 12 reports a facile and general catalytic method for the conversion of aryl bromides to arylamines, which works well for inter- and intramolecular processes. Further, it reports that this method include the experimental simplicity with tin/boron-free conditions, and has a broad substrate scope.

Article titled, "Nickel-catalyzed amination of aryl carbamates and sequential site-selective cross-couplings" by Tehetena Mesganaw, Amanda L. Silberstein, Stephen D. Ramgren, Noah F. Fine Nathel, Xin Hong, Peng Liu and Neil K. Garg in Chem. Sci., 2011, 2, 1766 reports the amination of aryl carbamates using nickel-catalysis. It also demonstrates that aryl carbamates are outstanding precursors for the synthesis of polysubstituted aryl amines using sequential carbamate functionalization/site-selective coupling processes.

Recent developments in transition-metal-free carbon-carbon and carbon-heteroatom bond-forming reactions utilizing a versatile class of reactive intermediates, viz., arynes, holds the potential for numerous applications in organic synthesis. Consequently, arynes have been employed for the construction of multisubstituted arenes with structural diversity and complexity. The versatile transition-metal-free applications of arynes include cycloaddition reactions, insertion reactions and multicomponent reactions. In addition, arynes have found applications in natural product synthesis.

Article titled, "Transition-metal-free α-Arylation of β-keto amides via an interrupted insertion reaction of arynes" by Kishor Mohanan, Yoann Coquerel, and Jean Rodriguez reported in *Org. Lett.,* 2012, 14 (17), pp 4686-4689 reports direct α-arylation reactions of secondary β-keto amides with arynes, generated by fluoride-induced elimination of ortho-silylaryltriflates. The transformation proceeds via an interrupted insertion reaction of arynes and leads to densely functionalized aromatic compounds exhibiting a chiral 'all carbon' quaternary center under transition-metal-free conditions.

There are several reports on transition-metal-catalyzed, synthesis of tertiary aryl amine derivatives, but the transition-metal free syntheses of tertiary arylamine derivatives are relatively rare. For example, a facile synthesis transition-metal-free procedure for the N-arylation of amines by Zhijian Liu et al reported in *J. Org. Chem.* 2006 Apr. 14; 71(8): 3198-3209 reports a reaction of amine with variety of o-silylaryl triflates in the presence of CsF in acetonitrile to yield the N-arylated amines. However, in the inventor's hands, synthesis of aryl amines were achieved using primary and secondary amines only, but using tert-amines, the arylation was not feasible. Despite these significant recent improvements, there still remains a need in the art to prepare tertiary arylamine derivatives in good yields utilizing the cheaper sources in cost effective manner.

OBJECTIVE OF THE INVENTION

The main object of the present invention is to provide a transition-metal-free process for N-arylation of tertiary amines using arynes generated in situ.

Another object of the present invention is to provide a coupling reaction between arynes generated in situ and tertiary amines derivatives leading to transition-metal-free synthesis of tertiary arylamines.

SUMMARY OF THE INVENTION

Accordingly, present invention provides a transition metal-free synthesis of tertiary arylamines compounds of general formula (I)

General formula I

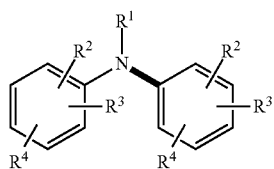

wherein
R1=ethyl, methyl or;

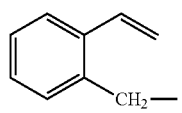

R2=H, alkyl (C1-C5), aryl (phenyl, C6-C8), halogen (F, Cl, Br, I), esters (C2-C4), CHO, CN, OH, CH=CH—COOEt, CH=CH—C6H4NO2, OCH3, OPh,

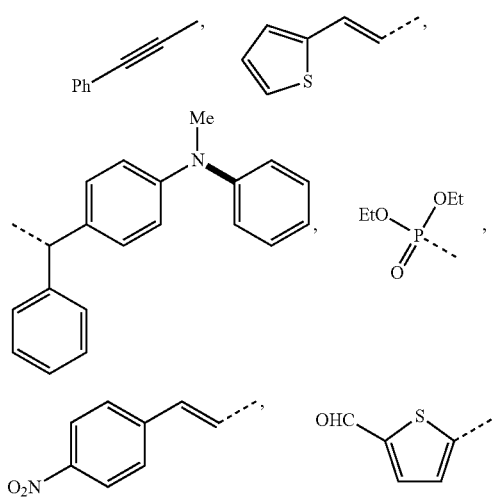

R3=H, CH$_3$, halogen (F, Cl, Br, I),
R4=H or D;
or R2+R3=—O—CH2-O—, —CH=CH—CH=CH—; —C(SO2Cl)=CH—CH=CH—;

comprising the steps of:

i. mixing 2-trimethylsilylaryl trifluoromethyl sulphonate of formula (II) and tertiary amine compounds of formula (III) in the ratio ranging between 2:1 to 1:2 in presence of 18-crown-6, KF and solvent (THF)

Formula II

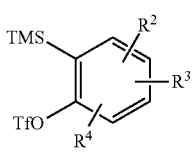

Formula III

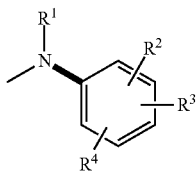

wherein $R^1$, $R^2$ and $R^3$ is as defined above.

In an embodiment of the present invention, the 2-trimethylsilylaryl trifluoromethyl sulphonate are selected from the group consisting of 3,6-dimethyl-2-(trimethylsilyl)phenyl trifluoromethanesulfonate, 4,5-dimethyl-2-(trimethylsilyl)phenyl trifluoromethanesulfonate, 6-(trimethylsilyl)benzo[d][1,3]dioxol-5-yl trifluoromethanesulfonate, 4,5-difluoro-2-(trimethylsilyl)phenyl trifluoromethanesulfonate, 3,6-dimethyl-2-(trimethylsilyl)phenyl trifluoromethanesulfonate, 2-methoxy-6-(trimethylsilyl)phenyl trifluoromethanesulfonate, 2-(trimethylsilyl)-naphthalen-1-yl trifluoromethanesulfonate, 4-methyl-2-(trimethylsilyl)-phenyl trifluoromethanesulfonate.

In another embodiment of the present invention, the tertiary amine compounds are selected from the group consisting of N,N-diethylaniline, N-methyl-N-phenylaniline, N,N-dimethylaniline, N,N,4-trimethylaniline, 3-(dimethylamino)phenol, 4-bromo-N,N-dimethyl aniline, 4-iodo-N,N-dimethyl aniline, 4-(dimethylamino)benzonitrile, ethyl 4-(dimethylamino)benzoate, 4-(dimethylamino)benzaldehyde, N,N,3-trimethylaniline, 3-bromo-N,N-dimethylaniline, methyl 2-(dimethylamino)benzoate, N,N,3,5-tetramethyl aniline, diethyl (4-(dimethylamino)benzyl) phosphonate, (E)-N,N-dimethyl-4-(2-(thiophen-2-yl)vinyl) aniline, N,N-dimethyl-4-(phenylethynyl)aniline, N,N-dimethyl naphthalen-1-amine, 5-(dimethyl-amino) naphthalene-1-sulfonyl chloride, 4,4'-(phenylmethylene)bis (N,N-dimethylaniline), ethyl (E)-3-(4-(dimethylamino) phenyl)acrylate, (E)-N,N-dimethyl-4-(4-nitrostyryl)-aniline, 5-(4-(dimethylamino)phenyl)thiophene-2-carbaldehyde, 3-(dimethylamino)phenol, 1,2,3,4-tetrahydroisoquinoline.

In yet another embodiment, present invention further comprises addition of 1.0 equiv ammonium bicarbonate (NH$_4$HCO$_3$) to increase the yield of tertiary arylamines.

In yet another embodiment of the present invention, the reaction is carried out at a temperature in the range of 58 to 62° C. for period in the range of 11 to 12 hours.

In yet another embodiment of the present invention, the coupling reaction is carried out under argon atmosphere.

DETAILED DESCRIPTION OF INVENTION

Figure 1:
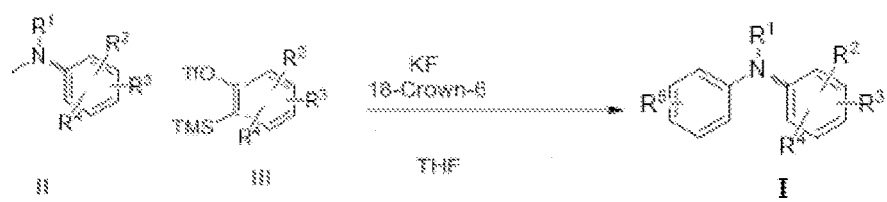
FIG. 1 represents transition metal free process for the synthesis of tertiary arylamine of general formula I.

The present invention provides a transition metal free method for the synthesis of tertiary arylamine of general formula I by the reaction of arynes generated by 2-trimethylsilylaryl trifluoromethyl sulphonate of formula II with tertiary amine of formula III in excellent yields. One preferred tertiary amine is N,N-dimethyl aniline.

Accordingly, present invention provides a transition metal-free process for the synthesis of tertiary arylamines compounds of general formula (I)

General Formula I

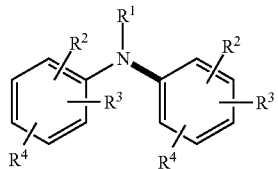

wherein
R1=ethyl, methyl or;

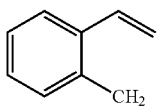

R2=H, alkyl (C1-C5), aryl (phenyl, C6-C8), halogen (F, Cl, Br, I), esters (C2-C4), CHO, CN, OH, CH=CH—COOEt, CH=CH—C6H4NO2, OCH3, OPh,

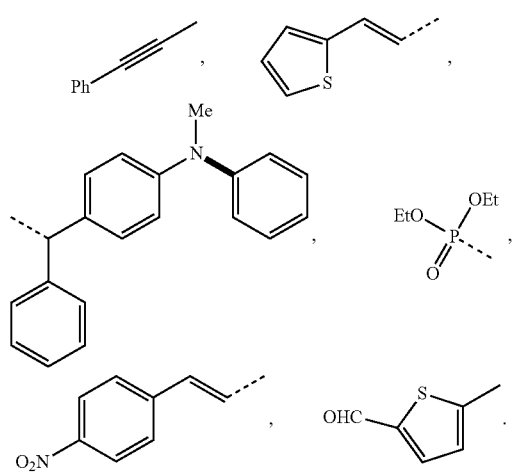

R3=H, CH$_3$, halogen (F, Cl, Br, I),
R4=H or D;
or R2+R3=—O—CH2-O—, —CH=CH—CH=CH—; —C(SO2Cl)=CH—CH=CH—;
comprising the steps of:
i. mixing aryne precursor 2-trimethylsilylaryl trifluoromethyl sulphonate of formula (II) and tertiary amines derivatives of formula (III) in presence of 18-crown-6, KF and solvent (THF) and optionally in the presence of a base at a temperature in the range of 58 to 62° C. preferably 60° C. under inert atmosphere for a period of 10-15 hrs preferably 12 hrs.

Formula II

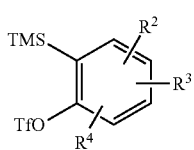

Formula III

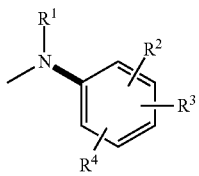

wherein R$^1$, R$^2$ and R$^3$ is as defined above;

The present invention provides a transition-metal-free synthesis of tertiary arylamines of general formula I further comprising of addition of ammonium bicarbonate (NH$_4$HCO$_3$) to increase the yield.

The aryne precursors 2-trimethylsilylaryl trifluoromethyl sulphonate of formula (II) are selected from the group comprising 3,6-dimethyl-2-(trimethylsilyl)phenyl trifluoromethanesulfonate, 4,5-dimethyl-2-(trimethylsilyl)phenyl trifluoromethanesulfonate, 6-(trimethylsilyl)benzo[d][1,3]dioxol-5-yl trifluoromethanesulfonate, 4,5-difluoro-2-(trimethylsilyl)phenyl tri-fluoromethanesulfonate, 3,6-dimethyl-2-(trimethylsilyl)phenyl trifluoromethanesulfonate, 2-methoxy-6-(trimethylsilyl)phenyl trifluoromethanesulfonate, 2-(trimethylsilyl)-naphthalen-1-yl trifluoromethanesulfonate, 4-methyl-2-(trimethylsilyl)-phenyl trifluoromethanesulfonate.

The tertiary amines of Formula III are selected from the group comprising of N,N-diethylaniline, N,N-dimethylaniline, N,N,4-trimethylaniline, 3-(dimethylamino)phenol, 4-bromo-N,N-dimethylaniline, 4-iodo-N,N-dimethyl aniline, 4-(dimethylamino)benzonitrile, ethyl 4-(dimethylamino)benzoate, 4-(dimethylamino)benzaldehyde, N,N,3-trimethylaniline, 3-bromo-N,N-dimethylaniline, methyl 2-(dimethylamino)benzoate, N,N,3,5-tetramethyl aniline, diethyl (4-(dimethylamino)benzyl)phosphonate, (E)-N,N-dimethyl-4-(2-(thiophen-2-yl)vinyl)aniline, N,N-dimethyl-4-(phenylethynyl)aniline, N,N-dimethyl naphthalen-1-amine, 5-(dimethyl-amino)naphthalene-1-sulfonyl chloride, 4,4'-(phenylmethylene)bis(N,N-dimethylaniline), ethyl (E)-3-(4-(dimethylamino)phenyl)acrylate, (E)-N,N-dimethyl-4-(4-nitrostyryl)-aniline, 5-(4-(dimethylamino)phenyl)thiophene-2-carbaldehyde, 3-(dimethylamino)phenol, 1,2,3,4-tetrahydroisoquinoline.

The invention further demonstrates the optimization of reaction conditions and molar ratios of the reactants along with the yields and tabulated below in table 1 and table 2.

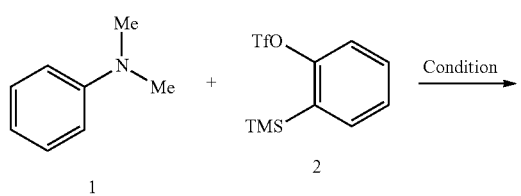

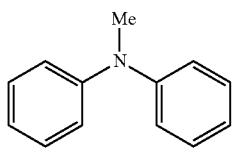

TABLE 1

| Sr. No. | equiv of 1 | equiv of 2 | Conditions | Yield of 3 (%) |
|---|---|---|---|---|
| 1 | 1.2 | 1 | KF (2.4 equiv), 18-Crown-6 (2.4 equiv), THF (1.0 mL), 60° C., 12 h. | 33 |
| 2 | 1.2 | 1 | KF (2.4 equiv), 18-Crown-6 (2.4 equiv), NH$_4$HCO$_3$ (1.0 equiv), THF (1.0 mL), 40° C., 12 h. | 88 |
| 3 | 1.2 | 1 | KF (2.4 equiv), 18-Crown-6 (2.4 equiv), NH$_4$HCO$_3$ (1.0 equiv), THF (1.0 mL), 60° C., 12 h. | 95 |
| 4 | 1.2 | 1 | TBAF (2.4 equiv), THF (1.0 mL), 60° C., 12 h. | 73 |
| 5 | 1.2 | 1 | TBAF (2.4 equiv), NaHCO$_3$ (1.0 equiv), THF (1.0 mL), 60° C., 12 h. | 78 |
| 6 | 1.2 | 1 | TBAF (2.4 equiv), NH$_4$HCO$_3$ (1.0 equiv), THF (1.0 mL), 60° C., 12 h. | 80 |
| 7 | 1 | 1.2 | TBAF (2.4 equiv), NH$_4$HCO$_3$ (1 equiv), THF (1.0 mL), 60° C., 12 h. | 75 |
| 8 | 1 | 1.2 | CsF (2.4 equiv), CH$_3$CN (1.0 mL), 60° C., 12 h | 6 |

TABLE 2

| Entry | variation from the standard conditions[a] | yield of 3 (%)[b] |
|---|---|---|
| 1 | None | 33 |
| 2 | CsF instead of KF and 18-crown-6, CH$_3$CN as the solvent | 6 |
| 3 | TBAF instead of KF and 18-crown-6 | 73[c] |
| 4 | (NH$_4$)HCO$_3$ 1.0 equiv as a additive with TBAF | 80[c] |
| 5 | (NH$_4$)HCO$_3$ 1.0 equiv as a additive with KF and 18-crown-6 | 98 (95)[d] |
| 6 | NaHCO$_3$ 1.0 equiv as a additive with KF and 18-crown-6 | 67 |
| 7 | H$_2$O 1.0 equiv as a additive with KF and 18-crown-6 | 70 |
| 8 | Reaction temperature 40° C. instead of 60° C. with (NH$_4$)HCO$_3$1.0 equiv as a additive | 88 |
| 9 | Reaction time 6 h instead of 12 h with (NH$_4$)HCO$_3$ 1.0 equiv as a additive | 78 |

[a]Standard conditions: 1 (0.25 mmol), 2 (0.30 mmol), KF (2.4 equiv), 18-crown-6 (2.4 equiv), THF (1.0 mL), 60° C. and 12 h.
[b]The yields were determined by $^1$H NMR analysis of crude products using CH$_2$Br$_2$ as the internal standard.
[c]Isolated yield at 0.25 mmol scale.
[d]Isolated yield at 0.50 mmol scale in parentheses.

As is evident from the above table, use of base facilitates the reaction and thus yield of the product (refer entry 1 and 2). It is further observed that the yield is higher at higher temperature when the other conditions are same (refer entry 2 and 3) and the appropriate molar ratio of compounds 1 and 2 observed to be in the range of 1:2 to 2:1 and product yield may vary in the range of 60-96%.

EXAMPLES

The following examples are given by way of illustration and therefore should not be construed to limit the scope of the invention.

Example 1

Figure 2:
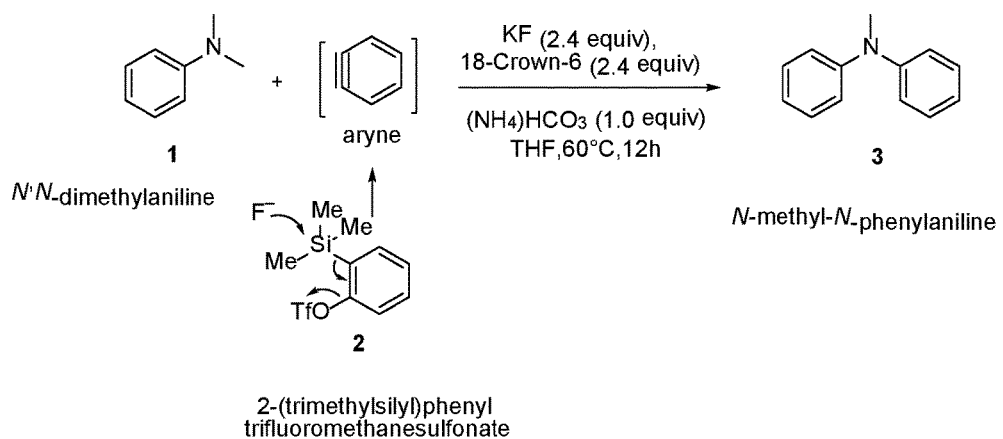
FIG. 2 represents synthesis of N-methyl-N-phenylaniline as in example 1.

Synthesis of N-methyl-N-phenylaniline (FIG. 2)

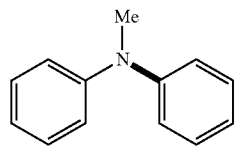

To a flame-dried screw-capped tube equipped with a magnetic stir bar were added 18-crown-6 (0.317 g, 1.2 mmol), KF (0.070 g, 1.2 mmol) and NH$_4$HCO$_3$ (0.040 g, 0.50, mmol). Then the screw-capped tube was evacuated and backfilled with argon. The mixture was dissolved in THF (2.0 mL) under argon atmosphere and then to the stirring solution were added the N, N-dimethylaniline 1 (0.061 g, 65 µL, 0.50 mmol) and 2-(trimethylsilyl)phenyltrifluoro-methanesulfonate 2 (0.179 g, 146 µL, 0.60 mmol) at room temperature (27° C.). Then the screw-capped tube kept in a preheated oil bath at 60° C. for 12 h. The reaction mixture cooled and the residue on column chromatography afforded N-methyl-N-phenylaniline 3 as a colourless oil (0.087 g, 95%).

R$_f$ (Pet. ether/DCM=90/10): 0.66; $^1$H NMR (400 MHz, CDCl$_3$) δ 7.28 (t, J=7.6 Hz, 4H), 7.03 (d, J=8.2 Hz, 4H), 6.96 (t, J=7.3 Hz, 2H), 3.32 (s, 3H). $^{13}$C NMR (100 MHz, CDCl$_3$): δ 149.18, 129.33, 121.39, 120.58, 40.38. HRMS (ESI) calculated [M+H]$^+$ for C$_{13}$H$_{14}$N: 184.1121. found: 184.1118. FTIR (cm$^{-1}$): 3036, 2929, 2879, 1591, 1496, 1342, 1271, 1253, 1186, 1156, 1131, 1092, 1074, 1029, 864, 750, 693.

Example 2

Figure 3:
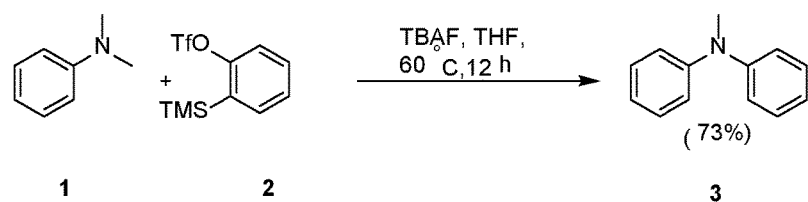
FIG. 3 represents synthesis of N-methyl-N-phenylaniline as in example 2.

Synthesis of N-methyl-N-phenylaniline in the absence of NH$_4$HCO$_3$ (FIG. 3)

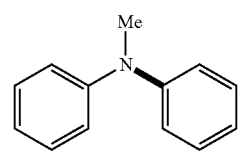

To a flame-dried screw-capped tube equipped with a magnetic stir bar were added N, N-dimethylaniline 1 (0.030 g, 32.0 µL, 0.25 mmol) and 2-(trimethylsilyl)phenyltrifluoromethanesulfonate 2 (0.090 g, 73 µL, 0.30 mmol). The mixture was dissolved in THF (1.0 mL) under argon atmosphere and then to the stirring solution was added the tetrabutyl ammonium fluoride (TBAF) (0.60 mL, 0.60 mmol) at room temperature (25° C.). Then the tube was kept in a preheated oil bath at 60° C. for 12 h. Usual processing of the reaction mixture followed by column chromatography of a crude reaction mixture afforded N-methyl-N-phenylaniline 3 as a colourless oil (0.033 g, 73%).

Example 3

Figure 4:
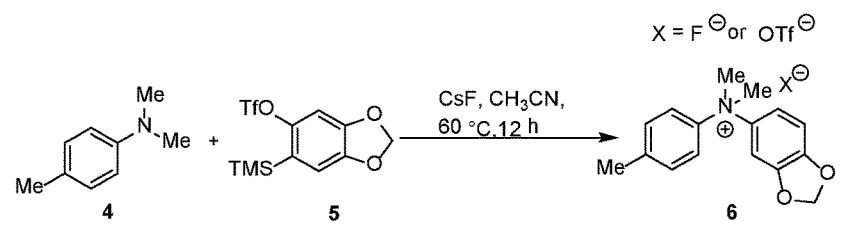
FIG. 4 represents synthesis of N,N-dimethyl-N-(p-tolyl) benzo[d][1,3]dioxol-4-aminium salt as in example 3.

Synthesis of N,N-dimethyl-N-(p-tolyl)benzo[d][1,3]dioxol-4-aminium salt (intermediate in this reaction) (FIG. 4)

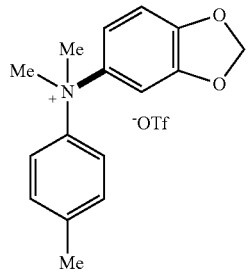

To a flame-dried screw-capped tube equipped with a magnetic stir bar was added dry CsF (0.095 g, 0.60 mmol) and then CH$_3$CN under argon atmosphere (1.0 mL). To the stirring solution N,N,4-trimethylaniline 4 (0.034 g, 37 μL, 0.25 mmol) and 6-(trimethylsilyl)benzo[d][1,3]dioxol-5-yl trifluoromethanesulfonate 5 (0.102 g, 0.3 mmol) were added at room temperature (27° C.). Then tube was kept in a preheated oil bath at 60° C. for 12 h. The reaction mixture cooled and the residue was purified by column chromatography to afford N,N-dimethyl-N-(p-tolypbenzo[d][1,3]dioxol-4-aminium salt 6 as a white solid. (0.100 g, 95%).

$^1$H NMR (400 MHz, CDCl$_3$) δ 7.40 (d, J=8.6 Hz, 2H), 7.29 (d, J=8.6 Hz, 2H), 7.18 (dd, J$_1$=8.8 Hz, J$_2$=2.6 Hz, 1H), 6.84 (d, J=8.8 Hz, 1H), 6.75 (d, J=2.6 Hz, 1H), 6.01 (s, 2H), 3.95 (s, 6H), 2.35 (s, 3H). $^{13}$C NMR (100 MHz, CDCl$_3$) 149.30, 149.14, 146.39, 142.56, 141.16, 131.18, 120.84, 114.84, 108.41, 103.02, 102.89, 58.99, 20.90. $^{19}$F NMR (376 MHz, CDCl$_3$) δ −78.41. HRMS (ESI) calculated [M]$^+$ for C$_{16}$H$_{18}$O$_2$N: 256.1332. found: 256.1334. FTIR (cm$^{-1}$): 3504, 3114, 3059, 3016, 2919, 1615, 1508, 1488, 1383, 1263, 1226, 1159, 1125, 1112, 1031, 971, 927, 898, 819, 756, 639.

Example 4

Synthesis of N,4-Dimethyl-N-phenylaniline

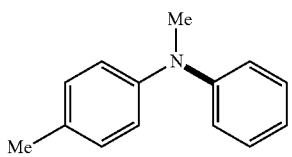

Following the general procedure, treatment of N,N,4-trimethylaniline (0.068 g, 73 μL, 0.50 mmol) with 2-(trimethylsilyl)phenyltrifluoromethanesulfonate (0.179 g, 146 μL, 0.60 mmol) in the presence of KF (0.070 g, 1.20 mmol), 18-crown-6 (0.317 g, 1.20 mmol) and (NH$_4$)HCO$_3$ (0.040 g, 0.50 mmol) in THF (2.0 mL) at 60° C. for 12 h followed by column chromatography (Pet. ether/DCM=98/02) afforded N,4-dimethyl-N-phenylaniline as a colorless oil (0.091 g, 92%).

R$_f$ (Pet. ether/DCM=90/10): 0.64; $^1$H NMR (400 MHz, CDCl$_3$) δ 7.29-7.25 (m, 2H), 7.16 (d, J=8.1 Hz, 2H), 7.04 (d, J=8.4 Hz, 2H), 6.98-6.95 (m, 2H), 6.91 (t, J=7.3 Hz, 1H), 3.33 (s, 3H), 2.37 (s, 3H). $^{13}$C NMR (100 MHz, CDCl$_3$) δ 149.50, 146.73, 132.19, 130.05, 129.15, 122.69, 119.93, 118.33, 40.46, 20.88. HRMS (ESI) calculated [M+H]$^+$ for C$_{14}$H$_{16}$N: 198.1277. found: 198.1275. FTIR (cm$^{-1}$): 3059, 3027, 2923, 2870, 1597, 1572, 1512, 1497, 1342, 1296, 1268, 1254, 1187, 1131, 1089, 1067, 868, 822, 751, 696.

Example 5

Synthesis of 4-Bromo-N-methyl-N-phenylaniline

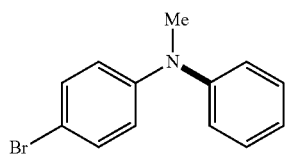

Following the general procedure, treatment of 4-bromo-N,N-dimethylaniline (0.100 g, 0.50 mmol) with 2-(trimethylsilyl)phenyl trifluoromethanesulfonate (0.179 g, 146 μL, 0.60 mmol) in the presence of KF (0.070 g, 1.20 mmol), 18-crown-6 (0.317 g, 1.20 mmol) and (NR$_4$)HCO$_3$ (0.040 g, 0.50 mmol) in THF (2.0 mL) at 60° C. for 12 h followed by column chromatography (Pet. ether/DCM=98/02) afforded 4-bromo-N-methyl-N-phenylaniline as a white solid (0.112 g, 85%).

R$_f$ (Pet. ether/DCM=90/10): 0.62; $^1$H NMR (400 MHz, CDCl$_3$) δ 7.34-7.29 (m, 4H), 7.07-7.01 (m, 3H), 6.84 (d, J=8.8 Hz, 2H), 3.29 (s, 3H). $^{13}$C NMR (100 MHz, CDCl$_3$) δ 148.67, 148.26, 132.07, 129.55, 122.71, 122.09, 120.71, 112.80, 40.42. HRMS (ESI) calculated [M+H]$^+$ for C$_{13}$H$_{13}$NBr: 262.0226. found: 262.0256. FTIR (cm$^{-1}$): 3062, 3037, 2926, 2882, 2815, 1583, 1489, 1454, 1343, 1254, 1185, 1133, 1119, 1075, 866, 815, 754, 734, 696 (C—Br).

Example 6

Synthesis of 4-Iodo-N-methyl-N-phenylaniline

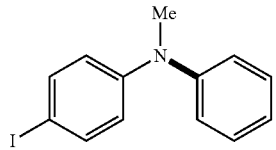

Following the general procedure, treatment of 4-iodo-N,N-dimethyl aniline (0.124 g, 0.50 mmol) with 2-(trimethylsilyl)phenyltrifluoromethanesulfonate (0.179 g, 146 μL, 0.60 mmol) in the presence of KF (0.070 g, 1.20 mmol), 18-crown-6 (0.317 g, 1.20 mmol) and (NH$_4$)HCO$_3$ (0.040 g, 0.50 mmol) in THF (2.0 mL) at 60° C. for 12 h followed by column chromatography (Pet. ether/DCM=98/02) afforded 4-iodo-N-methyl-N-phenylaniline as a white solid (0.131 g, 85%).

R$_f$ (Pet. ether/DCM=90/10): 0.64; $^1$H NMR (400 MHz, CDCl$_3$) δ 7.50 (d, J=8.8 Hz, 2H), 7.32 (t, J=8.2 Hz, 2H), 7.10-7.04 (m, 3H), 6.72 (d, J=8.8 Hz, 2H), 3.29 (s, 3H). $^{13}$C NMR (100 MHz, CDCl$_3$): δ 148.85, 148.46, 137.95, 129.60, 123.13, 122.68, 120.66, 82.20, 40.34. HRMS (ESI) calculated [M+H]+ for C$_{13}$H$_{13}$IN: 310.0092. found: 310.0100. FTIR (cm$^{-1}$): 3025, 2923, 2815, 1577, 1481, 1333, 1237, 1118, 1056, 805, 746, 687.

Example 7

Synthesis of 4-(Methyl (phenyl)amino)benzonitrile

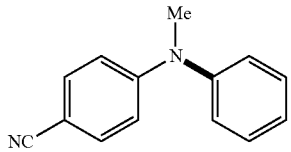

Following the general procedure, treatment of 4-(dimethylamino)benzonitrile (0.073 g, 0.50 mmol) with 2-(trimethylsilyl)phenyl trifluoromethanesulfonate (0.179 g, 146 μL, 0.60 mmol) in the presence of KF (0.070 g, 1.20 mmol), 18-crown-6 (0.317 g, 1.20 mmol) and (NH$_4$)HCO$_3$ (0.040 g, 0.50 mmol) in THF (2.0 mL) at 60° C. for 12 h followed by column chromatography (Pet. ether/EtOAc=98/01) afforded 4-(methyl(phenyl)amino)benzonitrile as a colorless oil (0.062 g, 60%).

R$_f$ (Pet. ether/EtOAc=95/05): 0.60; $^1$H NMR (400 MHz, CDCl$_3$) δ 7.46-7.42 (m, 4H), 7.30-7.21 (m, 3H), 6.74 (d, J=8.9 Hz, 2H), 3.36 (s, 3H). $^{13}$C NMR (100 MHz, CDCl$_3$) δ 152.04, 146.87, 133.35, 130.17, 126.56, 126.31, 120.48, 113.91, 99.40, 40.26. HRMS (ESI) calculated [M+H]+ for C$_{14}$H$_{13}$N$_2$: 209.1073. found: 209.1077. FTIR (cm$^{-1}$): 3061, 3039, 2946, 2886, 2215 (cyano group), 1609, 1591, 1513, 1494, 1355, 1257, 1176, 1142, 1119, 869, 823, 773, 701.

Example 8

Synthesis of Ethyl 4-(methyl (phenyl)amino)benzoate

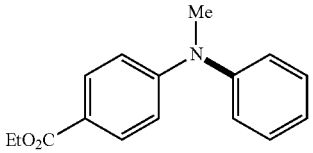

Following the general procedure, treatment of ethyl 4-(dimethylamino)benzoate (0.097 g, 0.50 mmol) with 2-(trimethylsilyl)phenyl trifluoromethanesulfonate (0.179 g, 146 μL, 0.60 mmol) in the presence of KF (0.070 g, 1.20 mmol), 18-crown-6 (0.317 g, 1.20 mmol) and (NH$_4$)HCO$_3$ (0.040 g, 0.50 mmol) in THF (2.0 mL) at 60° C. for 12 h followed by column chromatography (Pet. ether/EtOAc=99/01) afforded Ethyl 4-(methyl(phenyl)amino)benzoate as a colorless oil (0.110 g, 86%).

R$_f$ (Pet. ether/EtOAc=95/05): 0.63; $^1$H NMR (400 MHz, CDCl$_3$) δ 7.88 (d, J=8.9 Hz, 2H), 7.39 (t, J=7.8 Hz, 2H), 7.22-7.18 (m, 3H), 6.77 (d, J=8.9 Hz, 2H), 4.33 (q, J=7.1 Hz, 2H), 3.36 (s, 3H), 1.36 (t, J=7.1 Hz, 3H). $^{13}$C NMR (100 MHz, CDCl$_3$) δ 166.90, 152.57, 147.66, 131.06, 129.89, 125.89, 125.36, 119.67, 113.98, 60.41, 40.33, 14.57. HRMS (ESI) calculated [M+H]+ for C$_{16}$H$_{18}$O$_2$N: 256.1332. found: 256.1353. FTIR (cm$^{-1}$): 3061, 3038, 2980, 2820, 1705 (ester), 1609, 1591, 1567, 1515, 1495, 1351, 1314, 1276, 1181, 1107, 870, 840, 768, 730, 698.

Example 9

Synthesis of 4-(Methyl (phenyl)amino)benzaldehyde

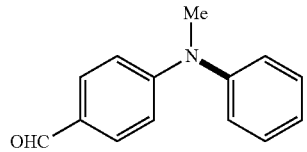

Following the general procedure, treatment of 4-(dimethylamino)benzaldehyde (0.075 g, 0.50 mmol) with 2-(trimethylsilyl)phenyl trifluoromethanesulfonate (0.179 g, 146 μL, 0.60 mmol) in the presence of KF (0.070 g, 1.20 mmol), 18-crown-6 (0.317 g, 1.20 mmol) and (NR$_4$)HCO$_3$ (0.040 g, 0.50 mmol) in THF (2.0 mL) at 60° C. for 12 h followed by column chromatography (Pet. ether/EtOAc=95/05) afforded 4-(methyl(phenyl)amino)benzaldehyde as a yellow solid (0.032 g, 30%).

R$_f$ (Pet. ether/EtOAc=90/10): 0.37; $^1$H NMR (400 MHz, CDCl$_3$) δ 9.76 (s, 1H), 7.69 (d, J=8.9 Hz, 2H), 7.44 (t, J=7.8 Hz, 2H), 7.28-7.27 (m, 1H), 7.23 (d, J=7.8 Hz, 2H), 6.78 (d, J=8.9 Hz, 2H), 3.39 (s, 3H). $^{13}$C NMR (100 MHz, CDCl$_3$) δ 190.52, 153.88, 147.00, 131.78, 130.13, 126.79, 126.67, 126.33, 113.51, 40.43. HRMS (ESI) calculated [M+H]+ for C$_{14}$H$_{14}$ON: 212.1070. found: 212.1074. FTIR (cm$^{-1}$): 3061, 3037, 2918, 2818, 2732, 1683, 1604, 1587, 1560, 1516, 1494, 1355, 1310, 1257, 1232, 1167, 1135, 1119, 1135, 1119, 1069, 1025, 872, 822, 769, 715, 699.

Example 10

Synthesis of N,3-Dimethyl-N-phenylaniline

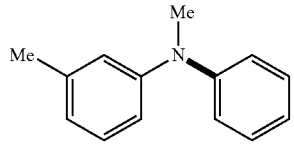

Following the general procedure, treatment of N,N,3-trimethylaniline (0.068 g, 72 μL, 0.50 mmol) with 2-(trimethylsilyl)phenyl trifluoromethanesulfonate (0.179 g, 146 μL, 0.60 mmol) in the presence of KF (0.070 g, 1.20 mmol), 18-crown-6 (0.317 g, 1.20 mmol) and (NH$_4$)HCO$_3$ (0.040 g, 0.50 mmol) in THF (2.0 mL) at 60° C. for 12 h followed by column chromatography (Pet. ether/DCM=98/02) afforded N,3-dimethyl-N-phenylaniline as a colorless oil (0.095 g, 96%).

R$_f$ (Pet. ether/DCM=90/10): 0.64; $^1$H NMR (400 MHz, CDCl$_3$) δ 7.30 (t, J=7.9 Hz, 2H), 7.20 (t, J=7.7 Hz, 1H), 7.04 (d, J=7.8 Hz, 2H), 6.97 (t, J=7.3 Hz, 1H), 6.89-6.87 (m, 2H), 6.83 (d, J=7.3 Hz, 1H), 3.34 (s, 3H), 2.34 (s, 3H). $^{13}$C NMR (100 MHz, CDCl$_3$) δ 149.27, 149.15, 139.14, 129.26, 129.16, 122.51, 121.60, 121.07, 120.24, 118.06, 40.40, 21.69. HRMS (ESI) calculated [M+H]+ for C$_{14}$H$_{16}$N: 198.1277. found: 198.1277. FTIR (cm$^{-1}$): 3037, 2920, 2811, 1594, 1583, 1495, 1456, 1344, 1262, 1191, 1172, 1127, 1094, 1071, 1029, 993, 922, 806, 751, 693.

Example 11

Synthesis of 3-Bromo-N-methyl-N-phenylaniline

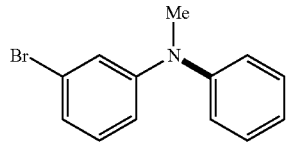

Following the general procedure, treatment of 3-bromo-N,N-dimethylaniline (0.100 g, 0.50 mmol) with 2-(trimethylsilyl)phenyl trifluoromethanesulfonate (0.179 g, 146 µL, 0.60 mmol) in the presence of KF (0.070 g, 1.20 mmol), 18-crown-6 (0.317 g, 1.20 mmol) and (NH$_4$)HCO$_3$ (0.040 g, 0.50 mmol) in THF (2.0 mL) at 60° C. for 12 h followed by column chromatography (Pet. ether/DCM=98/02) afforded 3-bromo-N-methyl-N-phenylaniline as a colorless oil (0.123 g, 94%).

$R_f$ (Pet. ether/DCM=90/10): 0.63; $^1$H NMR (400 MHz, CDCl$_3$) δ 7.37-7.33 (m, 2H), 7.13-7.06 (m, 5H), 6.99 (d, J=7.4 Hz, 1H), 6.84 (d, J=8.2 Hz, 1H), 3.31 (s, 3H). $^{13}$C NMR (100 MHz, CDCl$_3$) δ 150.54, 148.34, 130.35, 129.68, 123.60, 123.39, 123.15, 122.62, 120.54, 116.47, 40.39. HRMS (ESI) calculated [M+H]$^+$ for C$_{13}$H$_{13}$NBr: 262.0226. found: 262.0229. FTIR (cm$^{-1}$): 3402, 3062, 3037, 2927, 2814, 1586, 1560, 1495, 1481, 1343, 1247, 1133, 1101, 1081, 1070, 984, 887, 835, 760, 699 (C—Br).

Example 12

Synthesis of Methyl 2-(methyl(phenyl)amino)benzoate

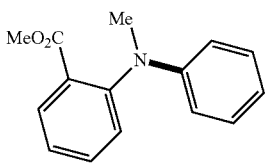

Following the general procedure, treatment of methyl 2-(dimethylamino)benzoate (0.090 g, 0.50 mmol) with 2-(trimethylsilyl)phenyl trifluoromethanesulfonate (0.179 g, 146 µL, 0.60 mmol) in the presence of KF (0.070 g, 1.20 mmol), 18-crown-6 (0.317 g, 1.20 mmol) and (NH$_4$)HCO$_3$ (0.040 g, 0.50 mmol) in THF (2.0 mL) at 60° C. for 12 h followed by column chromatography (Pet. ether/EtOAc=99/01) afforded methyl 2-(methyl(phenyl)amino)benzoate as a yellow oil (0.079 g, 65%).

$R_f$ (Pet. ether/EtOAc=95/05): 0.63; $^1$H NMR (400 MHz, CDCl$_3$) δ 7.81 (d, J=7.7 Hz, 1H), 7.54 (t, J=7.9 Hz, 1H), 7.30-7.27 (m, 2H), 7.18-7.15 (m, 2H), 6.75 (t, J=7.2 Hz, 1H), 6.65 (d, J=7.9 Hz, 2H), 3.60 (s, 3H), 3.29 (s, 3H). $^{13}$C NMR (100 MHz, CDCl$_3$) δ 167.62, 149.38, 148.25, 133.36, 131.54, 129.44, 129.15, 129.01, 125.35, 118.11, 114.40, 52.15, 40.47. HRMS (ESI) calculated [M+H]$^+$ for C$_{15}$H$_{16}$O$_2$N: 242.1176. found: 242.1176. FTIR (cm$^{-1}$): 3384, 3062, 3036, 2997, 2949, 2884, 2814, 1732 (ester), 1594, 1500, 1454, 1433, 1349, 1293, 1247, 1189, 1127, 1097, 1080, 1068, 991, 965, 871, 772, 749, 716, 693.

Example 13

Synthesis of N,3,5-trimethyl-N-phenylaniline

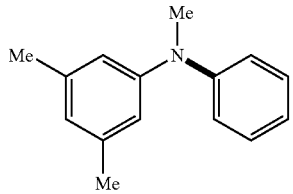

Following the general procedure, treatment of N,N,3,5-tetramethyl aniline (0.075 g, 82 µL, 0.50 mmol) with 2-(trimethylsilyl)phenyl trifluoromethanesulfonate (0.179 g, 146 µL, 0.60 mmol) in the presence of KF (0.070 g, 1.20 mmol), 18-crown-6 (0.317 g, 1.20 mmol) and (NH$_4$)HCO$_3$ (0.040 g, 0.50 mmol) in THF (2.0 mL) at 60° C. for 12 h followed by column chromatography (Pet. ether/DCM=98/02) afforded N,3,5-trimethyl-N-phenylaniline as a colorless oil (0.086 g, 81%).

$R_f$ (Pet. ether/DCM=90/10): 0.59; $^1$H NMR (400 MHz, CDCl$_3$) δ 7.32-7.28 (m, 2H), 7.03 (d, J 7.7 Hz, 2H), 6.96 (t, J=7.4 Hz, 1H), 6.72 (s, 2H), 6.68 (s, 1H), 3.32 (s, 3H), 2.30 (s, 6H). $^{13}$C NMR (100 MHz, CDCl$_3$): δ 149.33, 149.12, 138.97, 129.22, 123.72, 120.83, 119.98, 119.01, 40.46, 21.57. HRMS (ESI) calculated [M+H]$^+$ for C$_{15}$H$_{18}$N: 212.1439. found: 212.1442. FTIR (cm$^{-1}$): 3035, 2917, 2869, 2811, 1591, 1497, 1379, 1349, 1289, 1259, 1205, 1130, 1097, 1030, 1005, 992, 934, 847, 824, 785, 751, 693.

Example 14

Synthesis of Diethyl (4-(methyl(phenyl)amino)benzyl)phosphonate

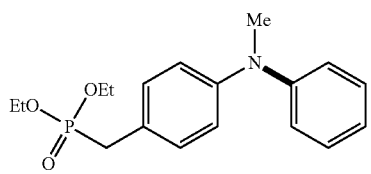

Following the general procedure, treatment of diethyl (4-(dimethylamino)benzyl)phosphonate (0.135 g, 0.50 mmol) with 2-(trimethylsilyl)phenyl trifluoromethanesulfonate (0.179 g, 146 µL, 0.60 mmol) in the presence of KF (0.070 g, 1.20 mmol), 18-crown-6 (0.317 g, 1.20 mmol) and (NH$_4$)HCO$_3$ (0.040 g, 0.50 mmol) in THF (2.0 mL) at 60° C. for 12 h followed by column chromatography (Pet. ether/EtOAc=50/50) afforded diethyl (4-(methyl(phenyl)amino)benzyl)phosphonate as a yellow oil (0.144 g, 87%).

$R_f$ (Pet. ether/EtOAc=40/60): 0.41; NMR (400 MHz, CDCl$_3$) δ 7.29 (t, J=8.1 Hz, 2H), 7.22 (dd, J$_1$=8.5 Hz, J$_2$=2.4 Hz, 2H), 7.03 (d, J=7.8 Hz, 2H), 6.99-6.96 (m, 3H), 4.09-4.02 (m, 4H), 3.32 (s, 3H), 3.12 (d, J=21.3 Hz, 2H), 1.29 (t, J=7.1, Hz, 6H). $^{13}$C NMR (100 MHz, CDCl$_3$) δ 149.06, 147.98 (d, J=3.26 Hz), 130.63 (d, J=6.65 Hz), 129.29, 123.97 (d, J=9.34 Hz), 121.47, 120.65, 120.48 (d, J=2.64

Hz), 62.21 (d, J=6.71 Hz), 40.34, 33.01 (d, J=139.1 Hz), 16.51 (d, J=5.91 Hz). HRMS (ESI) calculated [M+H]$^+$ for $C_{18}H_{25}O_3NP$: 334.1567. found: 334.1562. FTIR (cm$^{-1}$): 3463, 3299, 3059, 3033, 2982, 2930, 2907, 2814, 1596, 1571, 1513, 1497, 1452, 1391, 1366, 1343, 1252 (P=O), 1190, 1163, 1131, 1097, 1054, 1028, 962, 870, 850, 770, 754, 700.

Example 15

Synthesis of (E)-N-Methyl-N-phenyl-4-(2-(thiophen-2-yl)vinyl)aniline

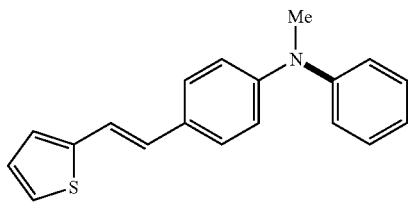

Following the general procedure, treatment of (E)-N,N-dimethyl-4-(2-(thiophen-2-yl)vinyl)aniline (0.057 g, 0.25 mmol) with 2-(trimethylsilyl)phenyl trifluoromethanesulfonate (0.089 g, 73 µL, 0.30 mmol) in the presence of KF (0.034 g, 0.60 mmol), 18-crown-6 (0.158 g, 0.60 mmol) and (NH$_4$)HCO$_3$ (0.020 g, 0.25 mmol) in THF (1.0 mL) at 60° C. for 12 h followed by column chromatography (Pet. ether/DCM=90/10) afforded (E)-N-methyl-N-phenyl-4-(2-(thiophen-2-yl)vinyl)aniline as a yellow solid (0.067 g, 93%).

R$_f$ (Pet. ether/DCM=80/20): 0.47; $^1$H NMR (400 MHz, CDCl$_3$) δ 7.37 (d, J=8.6 Hz, 2H), 7.33 (t, J=7.9 Hz, 2H), 7.16 (d, J=4.8 Hz, 1H), 7.13-7.10 (m, 3H), 7.06-7.03 (m, 2H), 7.01-6.99 (m, 1H), 6.96 (d, J=8.6 Hz, 2H), 6.90 (d, J=16.1 Hz, 1H), 3.55 (s, 3H). $^{13}$C NMR (100 MHz, CDCl$_3$) δ 148.69, 148.58, 143.62, 129.48, 129.30, 128.32, 127.66, 127.32, 125.31, 123.69, 122.61, 122.26, 119.44, 118.95, 40.36. HRMS (ESI) calculated [M+H]$^+$ for $C_{19}H_{18}NS$: 292.1154. found: 292.1184. FTIR (cm$^{-1}$): 3018, 2925, 1593, 1519, 1494, 1344, 1248, 1183, 1156, 1134, 1114, 1085, 954, 942, 858, 826, 759, 726, 692, 583, 501.

Example 16

Synthesis of N-Methyl-N-phenyl-4-(phenylethynyl)aniline

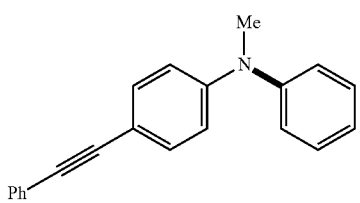

Following the general procedure; treatment of N,N-dimethyl-4-(phenylethynyl)aniline (0.111 g, 0.50 mmol) with 2-(trimethylsilyl)phenyltrifluoromethanesulfonate (0.179 g, 146 µL, 0.60 mmol) in the presence of KF (0.070 g, 1.20 mmol), 18-crown-6 (0.317 g, 1.20 mmol) and (NH$_4$)HCO$_3$ (0.040 g, 0.50 mmol) in THF (2.0 mL) at 60° C. for 12 h followed by column chromatography (Pet. ether/DCM=95/05) afforded N-methyl-N-phenyl-4-(phenylethynyl)aniline as a brown solid (0.116 g, 82%).

R$_f$ (Pet. ether/DCM=90/10): 0.57; NMR (400 MHz, CDCl$_3$) δ 7.52 (d, J=7.8 Hz, 2H), 7.41 (d, J=8.7 Hz, 2H), 7.38-7.30 (m, 5H), 7.17 (d, J=7.5 Hz, 2H), 7.11 (t, J=7.3 Hz, 1H), 6.87 (d, J=8.7 Hz, 2H), 3.55 (s, 3H). $^{13}$C NMR (100 MHz, CDCl$_3$) δ 149.01, 148.33, 132.68, 131.52, 129.65, 128.41, 127.84, 124.00, 123.91, 123.76, 116.91, 113.53, 90.22, 88.11, 40.28. HRMS (ESI) calculated [M+H]$^+$ for $C_{21}H_{18}N$: 284.1434. found: 284.1470. FTIR (cm$^{-1}$): 3058, 3036, 2927, 2815, 2211 (C—C triple bond), 1610, 1591, 1556, 1513, 1495, 1348, 1268, 1254, 1192, 1130, 1115, 1081, 1069, 1026, 869, 823, 755, 691.

Example 17

Synthesis of N-Methyl-N-phenylnaphthalen-1-amine

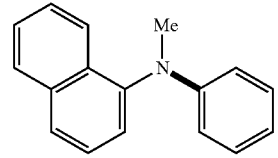

Following the general procedure, treatment of N,N-dimethyl naphthalen-1-amine (0.086 g, 83 µL, 0.50 mmol) with 2-(trimethylsilyl)phenyltrifluoromethanesulfonate (0.179 g, 146 µL, 0.60 mmol) in the presence of KF (0.070 g, 1.20 mmol), 18-crown-6 (0.317 g, 1.20 mmol) and (NH$_4$)HCO$_3$ (0.040 g, 0.50 mmol) in THF (2.0 mL) at 60° C. for 12 h followed by column chromatography (Pet. ether/DCM=98/02) afforded N-methyl-N-phenylnaphthalen-1-amine as a colourless oil (0.115 g, 98%).

R$_f$ (Pet. ether/DCM=90/10): 0.56; $^1$H NMR (400 MHz, CDCl$_3$) δ 7.93 (t, J=8.7 Hz, 2H), 7.83 (d, J=8.1 Hz, 1H), 7.55-7.51 (m, 2H), 7.46 (t, J=7.1 Hz, 1H), 7.40 (d, J=7.3 Hz, 1H), 7.20 (t, J=7.4 Hz, 2H), 6.77 (t, J=7.3 Hz, 1H), 6.66 (d, J=8.1 Hz, 2H), 3.43 (s, 3H). $^{13}$C NMR (100 MHz, CDCl$_3$) δ 150.22, 145.48, 135.25, 131.44, 129.05, 128.58, 126.76, 126.58, 126.47, 126.35, 125.37, 123.95, 117.32, 113.64, 40.32. HRMS (ESI) calculated [M+H]$^+$ for $C_{17}H_{16}N$: 234.1277. found: 234.1293. FTIR (cm$^{-1}$): 3058, 2931, 2881, 2811, 1600, 1575, 1498, 1453, 1394, 1338, 1297, 1266, 1243, 1187, 1140, 1106, 1032, 1010, 885, 867, 806, 776, 750, 693.

Example 18

Synthesis of 5-(Methyl(phenyl)amino)naphthalene-1-sulfonyl chloride

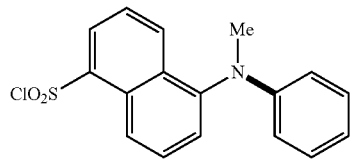

Following the general procedure, treatment of 5-(dimethylamino)naphthalene-1-sulfonyl chloride (0.067 g, 0.25 mmol) with 2-(trimethylsilyl)phenyl trifluoromethanesulfonate (0.149 g, 1214, 0.50 mmol) in the presence of KF (0.058 g, 1.0 mmol), 18-crown-6 (0.264 g, 1.0 mmol) and (NH$_4$)HCO$_3$ (0.020 g, 0.25 mmol) in THF (2.0 mL) at 60° C. for 12 h followed by column chromatography (Pet. ether/DCM=90/10) afforded 5-(methyl(phenyl)amino)naphthalene-1-sulfonyl chloride as a yellow oil (0.050 g, 61%).

$R_f$ (Pet. ether/DCM=80/20): 0.30; $^1$H NMR (400 MHz, CDCl$_3$) δ 8.49 (dd, J$_1$=8.7 Hz, J$_2$=2.6 Hz, 1H), 8.39-8.36 (m, 2H), 7.80 (t, J=8.1 Hz, 1H), 7.57-7.54 (m, 2H), 7.19 (t, J=8.0 Hz, 2H), 6.81 (t, J=7.3 Hz, 1H), 6.63 (d, J=7.9 Hz, 2H), 3.42 (s, 3H). $^{13}$C NMR (100 MHz, CDCl$_3$) δ 150.01, 147.01, 132.99, 132.47, 131.63, 131.62, 130.43, 130.10, 129.30, 126.89, 124.58, 122.59, 118.63, 114.54, 40.82. HRMS calculated [M]$^+$ for C$_{17}$H$_{14}$ClNO$_2$S: 331.0434. found: 331.0812. HRMS data was recorded on Synapt MALDI-MS (Waters, UK) using Synapt MALDI-MS (Waters, UK) or AB SCIEX TofTof™ 5800 using α-cyano-4-hydroxycinnamic acid as the solid matrix. FTIR (cm$^-$): 3329, 3061, 2928, 1600, 1572, 1498, 1415, 1400 (S=O), 1341, 1261, 1223, 1211 (S=O), 1148, 1110, 1044, 832, 792, 773, 748, 694, 640, 591.

Example 19

Synthesis of 4,4'-(Phenylmethylene)bis(N-methyl-N-phenylaniline

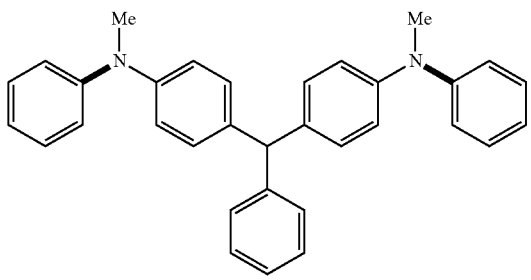

Following the general procedure, treatment of 4,4'-(phenylmethylene)bis(N,N-dimethylaniline) (0.082 g, 0.25 mmol) with 2-(trimethylsilyl)phenyl trifluoromethanesulfonate (0.179 g, 146 μL, 0.60 mmol) in the presence of KF (0.070 g, 1.20 mmol), 18-crown-6 (0.317 g, 1.20 mmol) and (NH$_4$)HCO$_3$ (0.040 g, 0.50 mmol) in THF (2.0 mL) at 60° C. for 12 h followed by column chromatography (Pet. ether/DCM=80/20) afforded 4,4'-(phenylmethylene)bis(N-methyl-N-phenylaniline) as a green oil (0.088 g, 78%).

$R_f$ (Pet. ether/DCM=80/20): 0.30; $^1$H NMR (400 MHz, CDCl$_3$) 7.30-7.17 (m, 9H), 7.05-7.00 (m, 8H), 6.96-6.91 (m, 6H), 5.44 (s, 1H), 3.29 (s, 6H). $^{13}$C NMR (100 MHz, CDCl$_3$): δ 149.13, 147.25, 144.70, 137.27, 130.20, 129.49, 129.25, 128.38, 126.27, 121.12, 120.48, 120.25, 55.72, 40.35. HRMS calculated [M+H]$^+$ for C$_{33}$H$_{30}$N$_2$: 455.2482. found: 455.1764. HRMS data was recorded on Synapt MALDI-MS (Waters, UK) using Synapt MALDI-MS (Waters, UK) or AB SCIEX TofTof™ 5800 using α-Cyano-4-hydroxycinnamic acid as the solid matrix. FTIR (cm$^{-1}$): 3083, 3058, 3026, 2935, 2876, 2841, 1594, 1568, 1496, 1451, 1342, 1298, 1273, 1253, 1186, 1156, 1131, 1117, 1086, 1067, 1029, 1016, 868, 820, 797, 752, 711, 697.

Example 20

Synthesis of Ethyl (E)-3-(4-(methyl (phenyl)amino) phenyl)acrylate

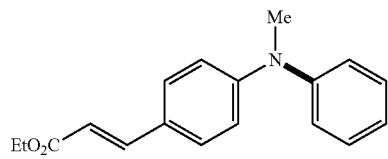

Following the general procedure, treatment of ethyl (E)-3-(4-(dimethylamino)phenyl)acrylate (0.110 g, 0.50 mmol) with 2-(trimethylsilyl)phenyl trifluoromethanesulfonate (0.179 g, 146 μL, 0.60 mmol) in the presence of KF (0.070 g, 1.20 mmol), 18-crown-6 (0.317 g, 1.20 mmol) and (NH$_4$)HCO$_3$ (0.040 g, 0.50 mmol) in THF (2.0 mL) at 60° C. for 12 h followed by column chromatography (Pet. ether/EtOAc=98/02) afforded Ethyl (E)-3-(4-(methyl(phenyl)amino)phenyl)acrylate as a yellow oil (0.130 g, 93%).

$R_f$ (Pet. ether/EtOAc=95/05): 0.50; NMR (400 MHz, CDCl$_3$) δ 7.63 (d, J=16.0 Hz, 1H), 7.40-7.35 (m, 4H), 7.19-7.14 (m, 3H), 6.82 (d, J=8.8 Hz, 2H), 6.25 (d, J=16.0 Hz, 1H), 4.25 (q, J=7.1 Hz, 2H), 3.35 (s, 3H), 1.33 (t, J=7.1 Hz, 3H). $^{13}$C NMR (100 MHz, CDCl$_3$) δ 167.83, 150.77, 147.88, 144.80, 129.77, 129.48, 125.03, 125.84, 124.68, 115.79, 113.98, 60.30, 40.28, 14.50. HRMS (ESI) calculated [M+H]$^+$ for C$_{18}$H$_{20}$O$_2$N: 282.1489. found: 282.1484. FTIR (cm$^{-1}$): 3061, 3035, 2980, 2936, 2902, 1705 (ester), 1628, 1606, 1591, 1559, 1515, 1495, 1350, 1330, 1258, 1215, 1166, 1137, 1122, 1040, 983, 868, 821, 768, 700.

Example 21

Synthesis of (E)-N-Methyl-4-(4-nitrostyryl)-N-phenylaniline

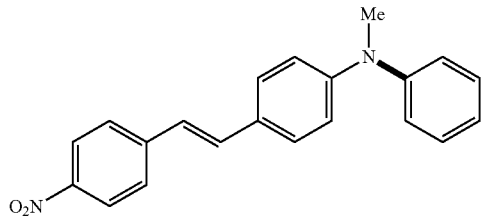

Following the general procedure, treatment of (E)-N,N-dimethyl-4-(4-nitrostyryl)aniline (0.067 g, 0.25 mmol) with 2-(trimethylsilyl)phenyl trifluoromethanesulfonate (0.090 g, 73 μL, 0.3 mmol) in the presence of KF (0.035 g, 0.6 mmol), 18-crown-6 (0.159 g, 0.6 mmol) and (NH$_4$)HCO$_3$ (0.020 g, 0.25 mmol) in THF (1.0 mL) at 60° C. for 12 h followed by column chromatography (Pet. ether/EtOAc=92/8) afforded (E)-N-Methyl-4-(4-nitrostyryl)-N-phenylaniline as a colourless oil (0.064 g, 78%).

$R_f$ (Pet. ether/EtOAc=90/10): 0.56; $^1$H NMR (400 MHz, CDCl$_3$) δ 8.10 (d, J=8.7 Hz, 2H), 7.49 (d, J=8.8 Hz, 2H), 7.34 (d, J=0.1=8.6 Hz, 2H), 7.28, (t, J=7.6 Hz, 2H) 7.17 (d, J=10.7 Hz, 1H), 7.11-7.08 (m, 2H), 7.04 (t, J=7.4 Hz, 1H), 6.88 (d, J=16.2 Hz, 1H), 6.83 (d, J=8.9 Hz, 2H), 3.28 (s, 3H). $^{13}$C NMR (100 MHz, CDCl$_3$) δ 149.70, 148.28, 146.29, 144.78, 133.38, 129.68, 128.23, 127.42, 126.43, 124.29, 123.97, 123.89, 123.09, 117.21, 40.35. HRMS calculated [M+H]+ for $C_{21}H_{19}O_2N_2$: 331.1441. found: 331.1438. FTIR (cm$^{-1}$): 2927, 1606, 1585, 1509 (NO$_2$), 1339 (NO$_2$), 1254, 1188, 1114, 971, 837, 806, 776, 749.

Example 22

Synthesis of 5-(4-(Methyl (phenyl)amino)phenyl)thiophene-2-carbaldehyde

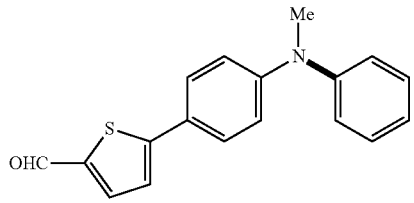

Following the general procedure, treatment of 5-(4-(dimethylamino)phenyl)thiophene-2-carbaldehyde (0.116 g, 0.50 mmol) with 2-(trimethylsilyl)phenyl trifluoromethanesulfonate (0.179 g, 146 μL, 0.60 mmol) in the presence of KF (0.070 g, 1.20 mmol), 18-crown-6 (0.317 g, 1.20 mmol) and (NH$_4$)HCO$_3$ (0.040 g, 0.50 mmol) in THF (2.0 mL) at 60° C. for 12 h followed by column chromatography (Pet. ether/EtOAc=90/10) afforded 5-(4-(methyl(phenyl)amino) phenyl)thiophene-2-carbaldehyde as a green colour solid (0.079 g, 54%).

R$_f$ (Pet. ether/EtOAc=90/10): 0.39; $^1$H NMR (400 MHz, CDCl$_3$) δ 9.86 (s, 1H), 7.71 (d, J=3.9 Hz, 1H), 7.56 (d, J=8.7 Hz, 2H), 7.40, (t, J=7.7 Hz, 2H) 7.29 (d, J=3.5 Hz, 1H), 7.22-7.16 (m, 3H), 6.91 (d, J=8.8 Hz, 2H), 3.39 (s, 3H). $^{13}$C NMR (100 MHz, CDCl$_3$) δ 182.66, 155.46, 150.21, 148.01, 140.86, 138.03, 129.79, 127.44, 124.64, 124.46, 123.65, 122.31, 116.58, 40.32. HRMS calculated [M+H]+ for $C_{18}H_{16}ONS$: 294.0947. found: 294.0941. FTIR (cm$^{-1}$): 3373, 2925, 2855, 2726, 1655 (CHO), 1590, 1458, 1377, 1231, 1081, 801, 773.

Example 23

Synthesis of N,3,4-trimethyl-N-phenylaniline

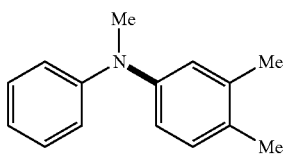

Following the general procedure, treatment of N,N-dimethylaniline (0.061 g, 65 μL, 0.50 mmol) with 4,5-dimethyl-2-(trimethylsilyl)phenyl trifluoromethanesulfonate (0.196 g, 0.60 mmol) in the presence of KF (0.070 g, 1.20 mmol), 18-crown-6 (0.317 g, 1.20 mmol) and (NH$_4$)HCO$_3$ (0.040 g, 0.50 mmol) in THF (2.0 mL) at 60° C. for 12 h followed by column chromatography (Pet. ether/DCM=96/4) afforded N,3,4-trimethyl-N-phenylaniline as a colourless oil (0.098 g, 93%).

R$_f$ (Pet. ether/DCM=90/10): 0.50; $^1$H NMR (400 MHz, CDCl$_3$) 87.30-7.26 (m, 2H), 7.13 (d, J=8.01 Hz, 1H), 6.98-6.89 (m, 5H), 3.34 (s, 3H), 2.29 (s, 3H), 2.28 (s, 3H). $^{13}$C NMR (100 MHz, CDCl$_3$) δ 149.51, 147.0, 137.68, 131.15, 130.55, 129.11, 124.31, 120.43, 119.64, 118.0, 40.49, 20.10, 19.21. HRMS calculated [M+H]+ for $C_{15}H_{18}N$: 212.1434. found: 212.1433. FTIR (cm$^{-1}$): 3022, 2920, 2809, 1595, 1496, 1450, 1343, 1300, 1117, 998, 751.

Example 24

Synthesis of N-methyl-N-phenylbenzo[d][1,3]dioxol-5-amine

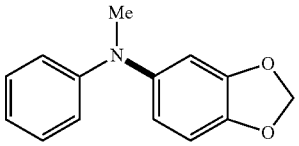

Following the general procedure, treatment of N,N-dimethylaniline (0.061 g, 65 μL, 0.50 mmol) with 6-(trimethylsilyl)benzo[d][1,3]dioxol-5-yl trifluoromethanesulfonate (0.205 g, 0.60 mmol) in the presence of KF (0.070 g, 1.20 mmol), 18-crown-6 (0.317 g, 1.20 mmol) and (NH$_4$)HCO$_3$ (0.040 g, 0.50, mmol) in THF (2.0 mL) at 60° C. for 12 h followed by column chromatography (Pet. ether/DCM=96/4) afforded N-methyl-N-phenylbenzo[d][1,3]dioxol-5-amine (0.106 g, 94%).

R$_f$ (Pet. ether/DCM=90/10): 0.33; $^1$H NMR (400 MHz, CDCl$_3$) δ 7.29-7.23 (m, 2H), 6.88-6.81 (m, 4H), 6.70-6.63 (m, 2H), 5.99 (s, 2H), 3.28 (s, 3H). $^{13}$C NMR (100 MHz, CDCl$_3$) δ 149.70, 148.39, 144.12, 143.80, 129.10, 119.11, 117.41, 116.69, 108.71, 106.31, 101.33, 40.78. HRMS calculated [M+H]+ for $C_{14}H_{14}O_2N$: 228.1019. found: 228.1013. FTIR (cm$^{-1}$): 2886, 2810, 1598, 1577, 1485, 1326, 1241, 1214, 1115, 1038, 939, 927, 751.

Example 25

Synthesis of 3,4-Difluoro-N-methyl-N-Phenylaniline

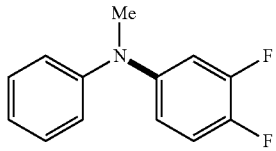

Following the general procedure, treatment of N,N-dimethylaniline (0.061 g, 65 μL, 0.50 mmol) with 4,5-difluoro-2-(trimethylsilyl)phenyl trifluoromethanesulfonate (0.201 g, 0.60 mmol) in the presence of KF (0.070 g, 1.20 mmol), 18-crown-6 (0.317 g, 1.20 mmol) and (NH$_4$)HCO$_3$ (0.040 g, 0.50, mmol) in THF (2.0 mL) at 60° C. for 12 h followed by column chromatography (Pet. ether/DCM=96/4) afforded 3,4-difluoro-N-methyl-N-phenylaniline 3w as a colorless oil (0.097 g, 88%).

R$_f$ (Pet. ether/DCM=90/10): 0.65; $^1$H NMR (400 MHz, CDCl$_3$) δ 7.89 (t, J=9.7 Hz, 2H), 7.57-7.52 (m, 4H), 7.25-7.18 (m, 1H), 7.09-7.04 (m, 1H), 2.85 (s, 3H). $^{13}$C NMR (100 MHz, CDCl$_3$) δ 170.75 (dd, J$_1$=16.8 Hz, J$_2$=307.5 Hz), 166.46, 163.69 (dd, J$_1$=16.5 Hz, J$_2$=302.0 Hz), 163.36 (dd, $J_1$=2.8 Hz, $J_2$=9.7 Hz), 142.67, 134.01, 132.17, 127.42 (d, J=21.4 Hz), 124.4 (q, J=3.07), 116.3 (d, J=24.2 Hz), 31.54. HRMS calculated [M+H]$^+$ for $C_{13}H_{12}NF_2$: 220.0932. found: 220.0930. FTIR (cm$^{-1}$): 3038, 2887, 2815, 1597, 1516, 1495, 1277 (C—F), 1119, 1083, 828, 774.

Example 26

Synthesis of N,2,5-trimethyl-N-Phenylaniline

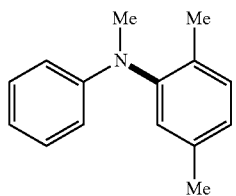

Following the general procedure, treatment of N,N-dimethylaniline (0.061 g, 65 μL, 0.50 mmol) with 3,6-dimethyl-2-(trimethylsilyl)phenyl trifluoromethanesulfonate (0.196 g, 0.60 mmol) in the presence of KF (0.070 g, 1.20 mmol), 18-crown-6 (0.317 g, 1.20 mmol) and $(NH_4)HCO_3$ (0.040 g, 0.50, mmol) in THF (2.0 mL) at 60° C. for 12 h followed by column chromatography (Pet. ether/DCM=96/4) afforded N,2,5-trimethyl-N-phenylaniline as a colorless oil (0.067 g, 64%).

$R_f$ (Pet. ether/DCM=90/10): 0.65; $^1$H NMR (400 MHz, CDCl$_3$) δ 7.22-7.18 (m, 3H), 7.03 (d, J=7.69 Hz, 1H), 6.99 (s, 1H), 6.73 (t, J=7.22 Hz, 1H), 6.73 (d, J=7.91 Hz, 2H), 3.23 (s, 3H) 2.33 (s, 3H), 2.12 (s, 3H). $^{13}$C NMR (100 MHz, CDCl$_3$) δ 149.31, 146.7, 137.32, 133.60, 131.24, 129.07, 128.93, 127.32, 127.32, 116.74, 112.88, 39.13, 20.99, 17.52. HRMS calculated [M+H]$^+$ for $C_{15}H_{18}N$: 212.1434. found: 212.1432. FTIR (cm$^-$): 3088, 3024, 2921, 2809, 1575, 1499, 1450, 1340, 1115, 1066, 815, 748.

Example 27

Synthesis of 3-Methoxy-N-methyl-N-Phenylaniline

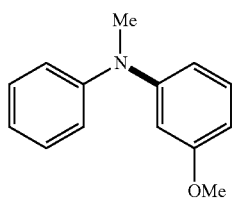

Following the general procedure, treatment of N,N-dimethylaniline (0.061 g, 65 μL, 0.50 mmol) with 2-methoxy-6-(trimethylsilyl)phenyl trifluoromethanesulfonate (0.197 g, 0.60 mmol) in the presence of KF (0.070 g, 1.20 mmol), 18-crown-6 (0.317 g, 1.20 mmol) and $(NH_4)HCO_3$ (0.040 g, 0.50, mmol) in THF (2.0 mL) at 60° C. for 12 h followed by column chromatography (Pet. ether/DCM=96/4) afforded 3-Methoxy-N-methyl-N-phenylaniline as a colorless oil (0.087 g, 95%).

$R_f$ (Pet. ether/DCM=90/10): 0.33; NMR (400 MHz, CDCl$_3$) δ 7.32 (t, J=8.1 Hz, 2H), 7.19 (d, J=7.9 Hz, 1H), 7.10 (d, J=7.9 Hz, 2H), 7.02, (t, J=7.5 Hz, 1H), 6.62 (d, J=8.3 Hz, 1H), 6.58 (s, 1H) 6.52 (d, J=7.9 Hz, 1H), 3.79 (s, 3H), 3.34 (s, 3H). $^{13}$C NMR (100 MHz, CDCl$_3$) δ 160.67, 150.50, 148.98, 129.88, 129.36, 122.11, 121.72, 112.33, 106.04, 105.72, 55.30, 40.42. HRMS calculated [M+H]$^+$ for $C_{14}H_{16}ON$: 214.1226. found: 214.1229. FTIR (cm$^{-1}$): 2999, 2936, 2834, 1595, 1494, 1437, 1436, 1347, 1169, 1127, 1049, 991, 754.

Example 28

Synthesis of N-Methyl-N-Phenylnaphthalen-2-amine

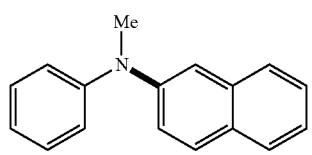

Following the general procedure, treatment of N,N-dimethylaniline (0.061 g, 65 μL, 0.50 mmol) with 2-(trimethylsilyl)naphthalen-1-yl trifluoromethanesulfonate (0.209 g, 0.60 mmol) in the presence of KF (0.070 g, 1.20 mmol), 18-crown-6 (0.317 g, 1.20 mmol) and $(NH_4)HCO_3$ (0.040 g, 0.50, mmol) in THF (2.0 mL) at 60° C. for 12 h followed by column chromatography (Pet. ether/DCM=96/4) afforded N-methyl-N-phenylnaphthalen-2-amine as a colorless oil (0.112 g, 96%).

$R_f$ (Pet. ether/DCM=90/10): 0.48; NMR (400 MHz, CDCl$_3$) δ 7.79 (d, J=8.18 Hz, 1H), 7.74 (t, J=7.7 Hz, 2H), 7.48-7.45 (m, 1H), 7.39-7.34 (m, 4H), 7.29-7.25 (m, 1H), 7.16 (d, J=7.74 Hz, 2H), 7.07 (t, J=7.25 Hz, 1H), 3.47 (s, 3H). $^{13}$C NMR (100 MHz, CDCl$_3$) δ 149.16, 146.68, 134.80, 129.42, 129.26, 128.71, 127.67, 126.87, 126.40, 123.87, 122.13. 121.92, 121.53, 114.74, 40.78. HRMS calculated [M+H]$^+$ for $C_{17}H_{16}N$: 234.1277. found: 234.1274. FTIR (cm$^{-1}$): 3056, 2940, 2811, 1628, 1593, 1494, 1364, 1297, 1281, 1321, 1119, 813, 747, 699.

Example 29

Synthesis of N,4-dimethyl-N-phenylaniline and N,3-dimethyl-N-phenylaniline

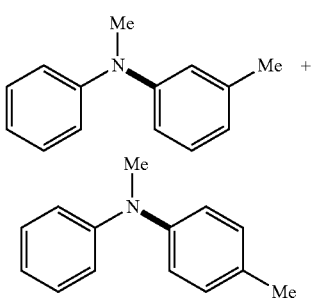

Following the general procedure, treatment of N,N-dimethylaniline (0.061 g, 65 μL, 0.50 mmol) with 4-methyl-2-(trimethylsilyl)phenyl trifluoromethanesulfonate (0.187 g, 0.60 mmol) in the presence of KF (0.070 g, 1.20 mmol), 18-crown-6 (0.317 g, 1.20 mmol) and $(NH_4)HCO_3$ (0.040 g, 0.50, mmol) in THF (2.0 mL) at 60° C. for 12 h followed by column chromatography (Pet ether/DCM=96/4) afforded N,4-dimethyl-N-phenylaniline and N,3-dimethyl-N-phenylaniline as a mixture of regioisomers in 1.3:1 ratio as a colorless oil (0.092 g, 93%).

$R_f$ (Pet ether/DCM=90/10): 0.55; $^1$H NMR (400 MHz, CDCl$_3$) of Major isomer; δ 7.35-7.31 (m, 2H), 7.24 (t, J=7.6 Hz, 1H), 7.09-7.08 (m, 2H), 6.96-6.91 (m, 3H), 6.87 (d, J=7.2 Hz, 1H), 3.37 (s, 3H), 2.37 (s, 3H). $^{13}$C NMR (100 MHz, CDCl$_3$) of Major isomer; δ 149.23, 149.12, 139.14, 129.15, 122.69, 121.57, 120.22, 118.28, 40.40, 21.70. $^1$H NMR (400 MHz, CDCl$_3$) of Minor isomer; δ 7.30-7.28 (m, 2H), 7.18 (d, J=8.20 Hz, 2H), 7.07-7.06 (m, 2H), 7.03-6.99 (m, 3H), 3.35 (s, 3H), 2.39 (s, 3H). $^{13}$C NMR (100 MHz, CDCl$_3$) of Minor isomer; δ 149.45, 146.68, 132.19, 130.04, 129.26, 122.49, 121.06, 119.91, 118.04, 40.46, 20.88. HRMS calculated [M+H]$^+$ for C$_{14}$H$_{16}$N: 198.1277. found: 198.1275. FTIR (cm$^{-1}$): 3026, 2920, 2874, 2810, 1595, 1509, 1342, 1260, 1129, 1090, 1028, 992.

Example 30

Synthesis of N-Methyl-N-(p-tolyl)benzo[d][1,3]dioxol-5-amine

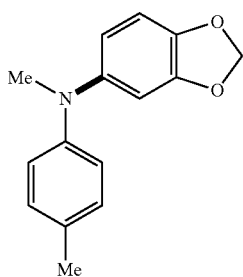

To a flame-dried round bottom flask equipped with a magnetic stir bar were added N,N dimethyl-N-(p-tolyl)benzo[d][1,3]dioxol-4-aminium salt (6.HOTf) (0.102 g, 0.25 mmol), 18-crown-6 (0.158 g, 0.60 mmol), KF (0.035 g, 0.60 mmol) and (NH$_4$)HCO$_3$ (0.020 g, 0.25 mmol) at room temperature (27° C.). Then the mixture was dissolved in THF (1.0 mL) under argon atmosphere and round bottom flask kept in a pre-heated oil bath at 60° C. for 12 h. The reaction mixture cooled and the residue on column chromatography (Pet. ether/DCM=90/10) afforded N-methyl-N-(p-tolyl)benzo[d][1,3]dioxol-5-amine as a colorless oil (0.043 g, 70%).

$R_f$ (Pet. ether/DCM=80/20): 0.32; $^1$H NMR (400 MHz, CDCl$_3$) δ 7.07 (d, J=8.3 Hz, 2H), 6.83 (d, J=8.3 Hz, 2H), 6.76 (d, J=8.3 Hz, 1H), 6.62 (d, J=2.1 Hz, 1H), 6.53 (dd, J$_1$=8.3 Hz, J$_2$=2.1 Hz, 1H), 5.94 (s, 2H), 3.23 (s, 3H), 2.30 (s, 3H). $^{13}$C NMR (100 MHz, CDCl$_3$) δ 148.30, 147.52, 144.58, 143.17, 129.76, 129.58, 118.67, 115.21, 108.56, 104.65, 101.17, 40.99, 20.63. HRMS (ESI) calculated [M+H]$^+$ for C$_{15}$H$_{16}$O$_2$N: 242.1176. found: 242.1162. FTIR (cm$^{-1}$): 2920, 2883, 2808, 1611, 1514, 1504, 1485, 1324, 1284, 1241, 1214, 1155, 1113, 1039, 940, 927, 841, 811, 781, 726.

Example 31

Synthesis of N,2,5-Trimethyl-N-phenylaniline-6-d

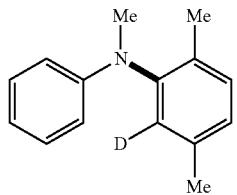

Following the general procedure, treatment of N,N-dimethylaniline (0.030 g, 32 μL, 0.25 mmol) with 3,6-dimethyl-2-(trimethylsilyl)phenyl trifluoromethanesulfonate (0.098 g, 0.30 mmol) in the presence of KF (0.035 g, 0.60 mmol), 18-crown-6 (0.158 g, 0.60 mmol) and D$_2$O (0.005 g, 4.6 μL, 0.25 mmol) in THF (1.0 mL) at 60° C. for 12 h followed by column chromatography (Pet. ether/EtOAc=99/01) afforded N,2,5-trimethyl-N-phenylaniline-6-d as a colorless oil (0.036 g, 69%).

$R_f$ (Pet. ether/DCM=90/10): 0.65; $^1$H NMR (400 MHz, CDCl$_3$) δ 7.22-7.18 (m, 3H), 7.04 (d, J=7.7 Hz, 1H), 7.00 (s, 32% H), 6.73 (t, J=7.9 Hz, 1H), 6.57 (d, J=7.9 Hz, 2H), 3.24 (s, 3H) 2.33 (s, 3H), 2.13 (s, 3H). $^{13}$C NMR (100 MHz, CDCl$_3$) δ 149.34, 146.73, 146.67, 137.32, 137.23, 133.60, 133.58, 131.24, 129.07, 128.92, 127.32, 116.77, 112.92, 39.15, 20.91, 17.51. HRMS(ESI) calculated [M+H]$^+$ for C$_{15}$H$_{17}$$^2$HN: 213.1497. found: 213.1490.

Example 32

Synthesis of 3-(Methyl(phenyl)amino)phenol, 3-Methoxy-N-methyl-N-phenylaniline and N-Methyl-3-phenoxy-N-phenylaniline Following the general procedure, treatment of 3-(dimethylamino)phenol (0.069 g, 0.50 mmol) with 2-(trimethylsilyl)phenyl trifluoromethanesulfonate (0.179 g, 146 μL, 0.60 mmol) in the presence of KF (0.070 g, 1.20 mmol), 18-crown-6 (0.317 g, 1.20 mmol) and (NH$_4$)HCO$_3$ (0.040 g, 0.50 mmol) in THF (2.0 mL) at 60° C. for 12 h followed by column chromatography afforded three product as follows, 3-(methyl(phenyl)amino)phenol as a brown oil (0.030 g, 30%), 3-methoxy-N-methyl-N-phenylaniline as a colorless oil (0.057 g, 53%), and N-methyl-3-phenoxy-N-phenylaniline as a colorless oil (0.020 g, 14%).

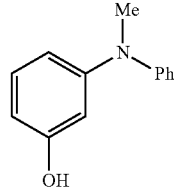 [SMILES: CN(c1ccccc1)c1cccc(O)c1]

3-(Methyl(phenyl)amino)phenol $R_f$ (Pet. ether/EtOAc=90/10): 0.30; $^1$H NMR (400 MHz, CDCl$_3$) δ 7.31 (t, J=7.9 Hz, 2H), 7.12-7.08 (m, 3H), 7.03 (t, J=7.4 Hz, 1H), 6.53 (dd, J$_1$=8.1 Hz, J$_2$=1.5 Hz, 1H), 6.44 (t, J=2.2 Hz, 1H), 6.39 (dd, J$_1$=8.1 Hz, J$_2$=2.3 Hz, 1H), 3.29 (s, 3H). $^{13}$C NMR (100 MHz, CDCl$_3$) δ 156.57, 150.71, 148.88, 130.11, 129.42, 122.59, 122.49, 111.43, 107.49, 105.90, 40.38. HRMS (ESI) calculated [M+H]$^+$ for C$_{13}$H$_{14}$ON: 200.1070. found: 200.1072. FTIR (cm$^{-1}$): 3381, 3060, 3037, 2929, 2814, 1591, 1496, 1459, 1349, 1275, 1195, 1165, 1126, 1092, 1027, 992, 955, 943, 829, 758, 693.

3-Methoxy-N-methyl-N-phenylaniline 3-(dimethylamino)phenol on reaction with 2-(trimethylsilyl)phenyl trifluoromethanesulfonate resulted in the formation of 3-(methyl(phenyl)amino)phenol, in situ, the free phenolic group is methylated or arylated to furnish the 3-methoxy-N-methyl-N-phenylaniline (Example No. 27) and N-methyl-3-phenoxy-N-phenylaniline (Example No. 28) respectively.

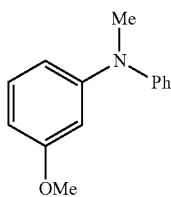 [SMILES: COc1cccc(N(C)c2ccccc2)c1]

R$_f$ (Pet. ether/DCM=90/10): 0.47; $^1$H NMR (400 MHz, CDCl$_3$) 7.31 (t, J=7.9 Hz, 2H), 7.19 (t, J=8.2 Hz, 1H), 7.10 (d, J=7.9 Hz, 2H), 7.02 (t, J=7.4 Hz, 1H), 6.61 (dd, J$_1$=8.1 Hz, J$_2$=1.8 Hz, 1H), 6.57 (t, J=2.2 Hz, 1H), 6.52 (dd, J$_1$=8.1, J$_2$=2.3 Hz, 1H), 3.78 (s, 3H), 3.33 (s, 3H). $^{13}$C NMR (100 MHz, CDCl$_3$) δ 160.66, 150.50, 148.98, 129.89, 129.36, 122.11, 121.73, 112.33, 106.04, 105.71, 55.30, 40.42. HRMS (ESI) calculated [M+H]$^+$ for C$_{14}$H$_{16}$ON: 214.1226. found: 214.1226. FTIR (cm$^{-1}$): 2999, 2932, 2834, 1592, 1493, 1467, 1347, 1274, 1215, 1169, 1127, 1094, 1048, 929, 754.

N-Methyl-3-phenoxy-N-phenylaniline

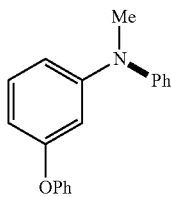

R$_f$ (Pet. ether/DCM=90/10): 0.50; $^1$H NMR (400 MHz, CDCl$_3$) δ 7.34-7.30 (m, 4H), 7.17 (t, J=8.1 Hz, 1H), 7.12 (d, J=7.8 Hz, 2H), 7.08 (t, J=7.4 Hz, 1H), 7.05-7.02 (m, 3H), 6.69 (dd, J$_1$=8.2 Hz, J$_2$=1.5 Hz, 1H), 6.67 (t, J=2.0 Hz, 1H), 6.51 (dd, J$_1$=8.2, J$_2$=1.5 Hz, 1H), 3.30 (s, 3H). $^{13}$C NMR (100 MHz, CDCl$_3$) δ 158.12, 157.44, 150.75, 148.70, 130.03, 12937, 129.49, 123.15, 122.87, 122.68, 118.84, 113.63, 110.50, 109.33, 40.41. HRMS (ESI) calculated [M+H]$^+$ for C$_{19}$H$_{18}$ON: 276.1383. found: 276.1385. FTIR (cm$^{-1}$): 3063, 3038, 2925, 2814, 1588, 1488, 1347, 1260, 1222, 1163, 1125, 1092, 1072, 1024, 993, 959, 847, 769, 754, 691.

Example 33

Synthesis of N-Ethyl-N-phenylaniline

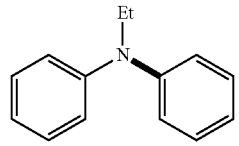

Following the general procedure, treatment of N,N-diethylaniline (0.075 g, 81 μL, 0.50 mmol) with 2-(trimethylsilyl)phenyl trifluoromethanesulfonate (0.179 g, 146 μL, 0.60 mmol) in the presence of KF (0.070 g, 1.20 mmol), 18-crown-6 (0.317 g, 1.20 mmol) in THF (2.0 mL) at 60° C. for 12 h followed by column chromatography (Pet. ether/DCM=98/02) afforded N-Ethyl-N-phenylaniline as a colorless oil (0.060 g, 61%).

R$_f$ (Pet. ether/DCM=90/10): 0.66; $^1$H NMR (400 MHz, CDCl$_3$) δ 7.28-7.25 (m, 4H), 7.00 (d, J=7.5 Hz, 4H), 6.94 (t, J=7.4 Hz, 2H), 3.80-3.76 (m, 2H), 1.24-1.21 (m, 3H). $^{13}$C NMR (100 MHz, CDCl$_3$) δ 147.89, 129.38, 121.22, 121.06, 46.54, 12.82. HRMS (ESI) calculated [M+H]$^+$ for C$_{14}$H$_{16}$N: 198.1277. found: 198.1277. FTIR (cm$^{-1}$): 3060, 3036, 2972, 2929, 2870, 1588, 1495, 1371, 1348, 1261, 1241, 1131, 1100, 783, 748, 693.

Example 34

Synthesis of N-Phenyl-N-(2-vinylbenzyl)aniline

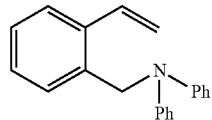 [SMILES: C=Cc1ccccc1CN(c1ccccc1)c1ccccc1]

Treatment of 1,2,3,4-tetrahydroisoquinoline (0.033 g, 32 μL, 0.25 mmol) with 2-(trimethylsilyl)phenyl trifluoromethanesulfonate (0.179 g, 146 μL, 0.60 mmol) in the presence of KF (0.070 g, 1.20 mmol) and 18-crown-6 (0.317 g, 1.20 mmol) in THF (2.0 mL) at 60° C. for 12 h followed by column chromatography (Pet. ether/DCM=98/02) afforded N-phenyl-N-(2-vinylbenzyl)aniline as a white solid (0.060 g, 86%).

R$_f$ (Pet. ether/DCM=90/10): 0.65; $^1$H NMR (400 MHz, CDCl$_3$) δ 7.50 (d, J=7.0 Hz, 1H), 7.42 (d, J=7.0 Hz, 1H), 7.27-7.18 (m, 6H), 7.07 (d, J=7.9 Hz, 4H), 7.02-6.94 (m, 3H), 5.68 (d, J=17.3 Hz, 1H), 5.37 (d, J=11.0 Hz, 1H), 5.04 (s, 2H). $^{13}$C NMR (100 MHz, CDCl$_3$) δ 148.06, 136.10, 135.49, 133.76, 129.40, 128.07, 127.08, 126.85, 126.23, 121.59, 120.77, 116.66, 54.37. HRMS (ESI) calculated [M+H]$^+$ for C$_{21}$H$_{20}$N: 286.1595. found: 286.1592. FTIR (cm$^{-1}$): 3061, 3028, 2921, 2853, 1579, 1485, 1338, 1227, 1062, 986, 914, 848.

ADVANTAGES OF THE INVENTION

1. Transition-Metal free approach.
2. High yields.
3. Use of Simple and easily available starting materials.

4. Synthesis of Arylamines which play a key role in a number of fields like Pharmaceuticals, Agrochemicals, Dyes, Electronic materials.

We claim:

1. A transition metal-free synthesis of tertiary arylamines compounds of general formula (I)

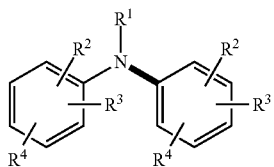

General Formula I wherein

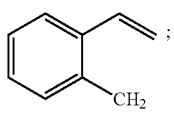

$R^1$=ethyl, methyl or $R^2$=H, alkyl ($C_1$-$C_5$), $C_6$-$C_8$-aryl, halogen (F, Cl, Br, I), —C(O)(OCH$_3$), —C(O)(OCH$_2$CH$_3$), CHO, CN, OH, CH=CH—COOEt, CH=CH—$C_6H_4NO_2$, OCH$_3$, OPh,

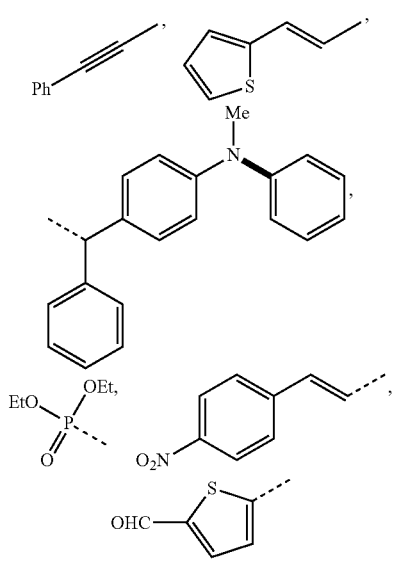

$R^3$=H, CH3, halogen (F, Cl, Br, I),
$R^4$=H or D;
or $R^2$+$R^3$=—O—CH2-O—, —CH=CH—CH=CH—; —C(SO2Cl)=CH—CH=CH—;

comprising the steps of:

i. mixing 2-trimethylsilylaryl trifluoromethyl sulphonate of formula (II) and tertiary amine compounds of formula (III) in the ratio ranging between 2:1 to 1:2 in presence of 18-crown-6, KF and solvent (THF)

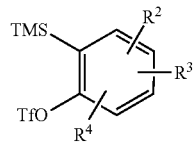

Formula II

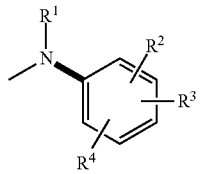

Formula III wherein $R^1$, $R^2$ and $R^3$ is as defined above.

2. The process according to claim 1, wherein the 2-trimethylsilylaryl trifluoromethyl sulphonate are selected from the group consisting of 3,6-dimethyl-2-(trimethylsilyl)phenyl trifluoromethanesulfonate, 4,5-dimethyl-2-(trimethylsilyl)phenyl trifluoromethanesulfonate, 6-(trimethylsilyl)benzo[d][1,3]dioxol-5-yl trifluoromethanesulfonate, 4,5-difluoro-2-(trimethylsilyl)phenyl trifluoromethanesulfonate, 3,6-dimethyl-2-(trimethylsilyl)phenyl trifluoromethanesulfonate, 2-methoxy-6-(trimethylsilyl)phenyl trifluoromethanesulfonate, 2-(trimethylsilyl)-naphthalen-1-yl trifluoromethanesulfone, 4-methyl-2-(trimethylsilyl)-phenyl trifluoromethanesulfonate.

3. The process according to claim 1, wherein the tertiary amine compounds are selected from the group consisting of N, N-diethylaniline, N-methyl-N-phenylaniline, N,N-dimethylaniline, N,N,4-trimethylaniline, 3-(dimethylamino)phenol, 4-bromo-N,N-dimethylaniline, 4-iodo-N,N-dimethyl aniline, 4-(dimethyl amino) benzonitrile, ethyl 4-(dimethylamino)benzoate, 4-(dimethylamino) benzaldehyde, N,N,3-trimethylaniline, 3-bromo-N,N-dimethylaniline, methyl 2-(dimethylamino)benzoate, N,N,3,5-tetramethyl aniline, diethyl (4-(dimethylamino)benzyl) phosphonate (E)-N,N-dimethyl-4-(2-(thiophen-2-yl)vinyl)aniline, N,N-dimethyl-4-(phenyl ethynyl)aniline, N,N-dimethyl naphthalene-1-amine, 5-(dimethyl-amino) naphthalene-1-sulfonyl chloride, 4,4'-(phenylmethylene)bis (N,N-dimethylaniline), ethyl (E)-3-(4-(dimethylamino)phenyl)acrylate, (E)-N,N-dimethyl-4-(4-nitrostyryl)-aniline, 5-(4-(dimethylamino)phenyl)thiophene-2-carbaldehyde, and 3-(dimethylamino)phenol.

4. The process according to claim 1, further comprises addition of 1.0 equiv ammonium bicarbonate ($NH_4HCO_3$) to increase the yield of tertiary arylamines.

5. The process according to claim 1, wherein the reaction is carried out at a temperature in the range of 58 to 62° C. for period in the range of 11 to 12 hours.

6. The process according to claim 1, wherein the coupling reaction is carried out under argon atmosphere.

* * * * *